United States Patent
Kanayama et al.

(10) Patent No.: US 9,897,599 B2
(45) Date of Patent: Feb. 20, 2018

(54) SPECIMEN MEASUREMENT APPARATUS AND SPECIMEN MEASUREMENT METHOD

(71) Applicant: Toshiba Medical Systems Corporation, Otawara-shi (JP)

(72) Inventors: Shoichi Kanayama, Otawara (JP); Isao Nawata, Otawara (JP); Ichiro Tono, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/814,808

(22) Filed: Jul. 31, 2015

(65) Prior Publication Data

US 2016/0041160 A1 Feb. 11, 2016

(30) Foreign Application Priority Data

Aug. 5, 2014 (JP) .................................. 2014-159808

(51) Int. Cl.
| | | |
|---|---|---|
| *G01N 33/543* | (2006.01) | |
| *G01N 21/77* | (2006.01) | |
| *G01N 21/82* | (2006.01) | |
| G01N 21/552 | (2014.01) | |
| G01N 21/17 | (2006.01) | |
| G01N 21/75 | (2006.01) | |
| G01N 21/27 | (2006.01) | |

(52) U.S. Cl.
CPC ... *G01N 33/54373* (2013.01); *G01N 21/7703* (2013.01); *G01N 21/82* (2013.01); *G01N 21/272* (2013.01); *G01N 21/552* (2013.01); *G01N 2021/1727* (2013.01); *G01N 2021/1731* (2013.01); *G01N 2021/757* (2013.01)

(58) Field of Classification Search
None
See application file for complete search history.

(56) References Cited

U.S. PATENT DOCUMENTS

| | | | |
|---|---|---|---|
| 4,621,059 A | 11/1986 | Rokugawa | |
| 5,341,215 A * | 8/1994 | Seher | ................... G01N 21/553 356/445 |
| 2011/0217698 A1* | 9/2011 | Rank | ........................ C12Q 1/25 435/6.1 |

FOREIGN PATENT DOCUMENTS

| | | |
|---|---|---|
| CN | 1335465 A | 2/2002 |
| CN | 1643370 A | 7/2005 |
| CN | 101536368 A | 9/2009 |
| CN | 101790685 A | 7/2010 |

(Continued)

OTHER PUBLICATIONS

Chinese Office Action dated Aug. 1 2017 in Chinese Application No. 201510471155.8 (7 pages).

*Primary Examiner* — Rebecca L Martinez
(74) *Attorney, Agent, or Firm* — Oblon, McClelland, Maier & Neustadt, L.L.P.

(57) ABSTRACT

According to one embodiment, a specimen measurement apparatus includes a detector and a control circuit, and is configured to perform a plurality of steps to measure the properties of a test substance retained in a reaction container. The detector outputs electromagnetic waves to the reaction container and detects the electromagnetic waves that vary according to the state in the reaction container. The control circuit controls transition timing between steps of the plurality of steps based on the detection result of the electromagnetic waves obtained by the detector.

13 Claims, 20 Drawing Sheets

(56) References Cited

FOREIGN PATENT DOCUMENTS

| | | |
|---|---|---|
| CN | 102422144 A | 4/2012 |
| CN | 102995803 A | 3/2013 |
| JP | 2-281143 | 11/1990 |
| JP | 2005-77338 | 3/2005 |

* cited by examiner

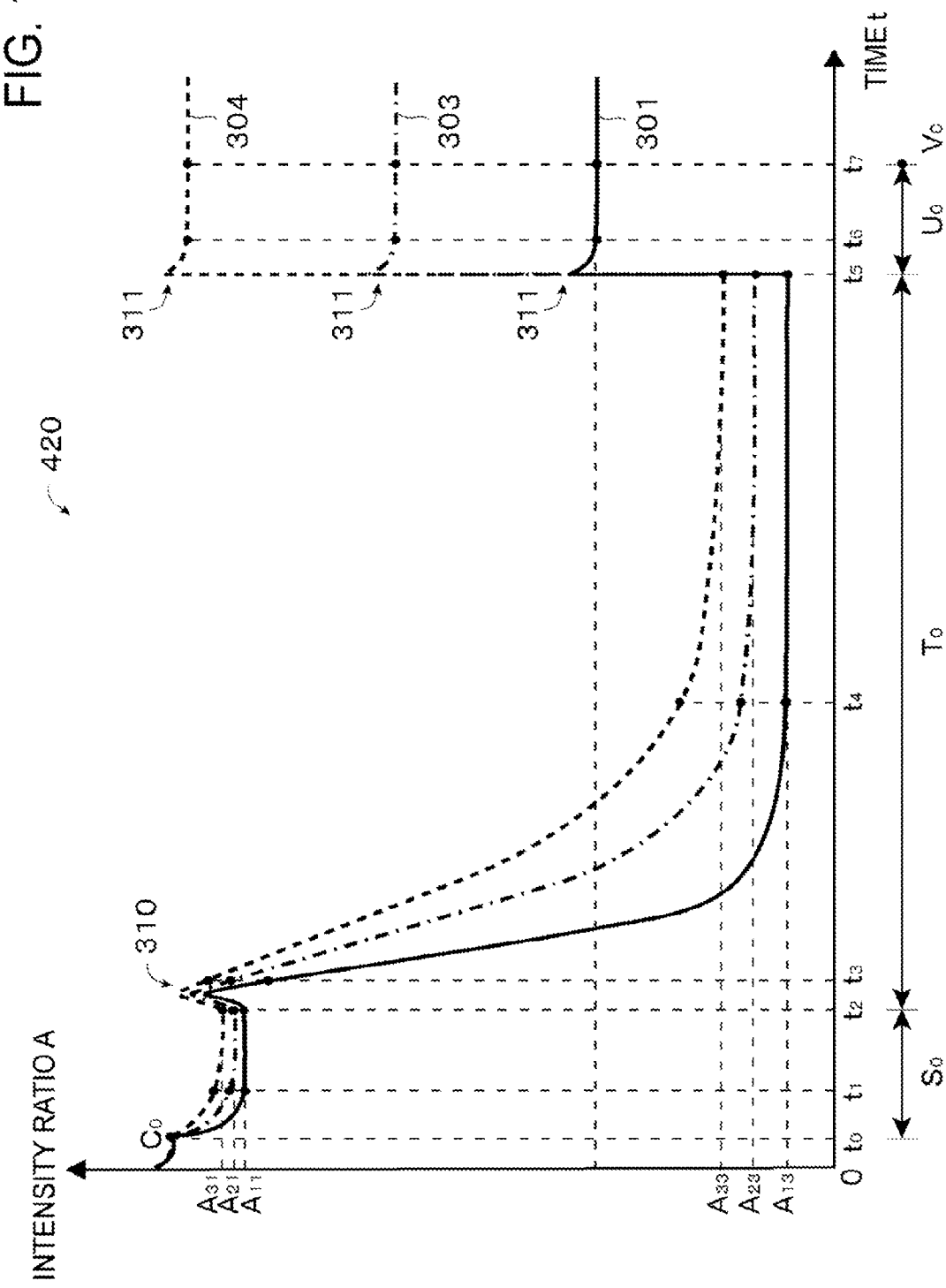

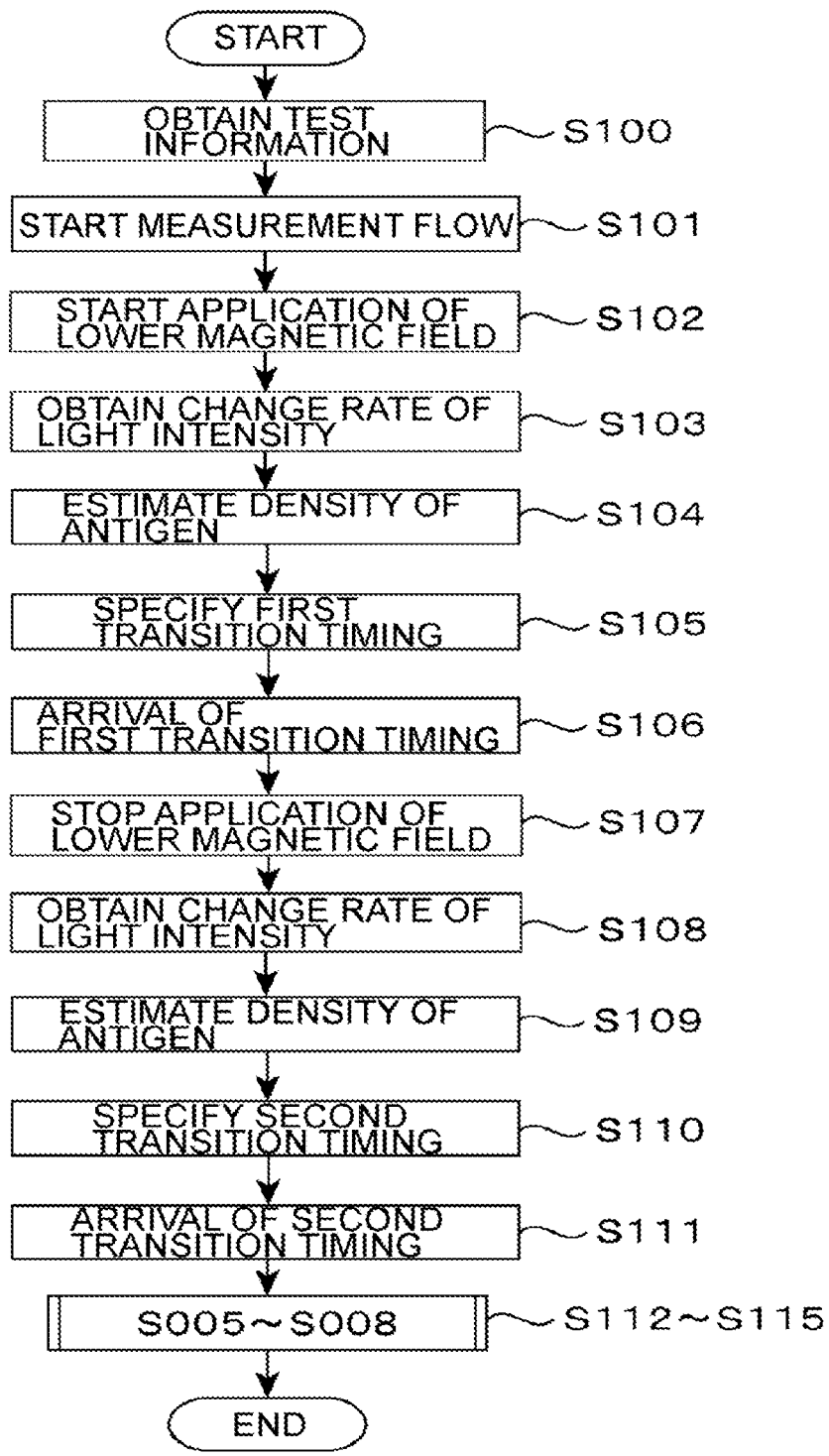

SPECIMEN MEASUREMENT APPARATUS AND SPECIMEN MEASUREMENT METHOD

CROSS-REFERENCE TO RELATED APPLICATION

This application is based upon and claims the benefit of priority from Japanese Patent Application No. 2014-159808, filed on Aug. 5, 2014; the entire contents of which are incorporated herein by reference.

FIELD

Embodiments described herein relate generally to a specimen measurement apparatus and a specimen measurement method.

BACKGROUND

A specimen measurement apparatus is used to analyze a test sample prepared from a specimen and a reagent to thereby detect an objective substance in the specimen qualitatively or quantitatively. The specimen measurement apparatus measures the test sample optically or electrically.

For example, the specimen measurement apparatus optically measures the test sample, and detects an immunologically active substance such as antigen and antibody in the specimen. This immunological test includes a plurality of steps, and the time required for each step is determined in advance.

The required times for these steps are often determined uniformly to guarantee the measurement sensitivity. Therefore, depending on a test substance or a test item, the sufficient time required to achieve the object of a step may be less than a set time determined in advance. However, the required time for the step is not changed from the set time even in such a case, and accordingly, is longer than the sufficient time required. In this way, in the conventional immunological test, the steps do not always flow well from one to the next at a suitable timing, and thus the test may take more time than necessary.

BRIEF DESCRIPTION OF THE DRAWINGS

FIG. 15 is a graph illustrating a time-series variation in the intensity ratio of output light; and FIG. 16 is a flowchart of another example of the operation of the specimen measurement apparatus in the third embodiment.

DETAILED DESCRIPTION

In general, according to one embodiment, a specimen measurement apparatus includes a detector and a control circuit, and is configured to perform a plurality of steps to measure the properties of a test substance retained in a reaction container. The detector outputs electromagnetic waves to the reaction container and detects the electromagnetic waves that vary according to the state in the reaction container. The control circuit controls transition timing between steps of the plurality of steps based on the detection result of the electromagnetic waves obtained by the detector.

According to another embodiment, a specimen measurement method includes measuring the properties of a test substance retained in a reaction container by a plurality of steps. The specimen measurement method includes outputting electromagnetic waves to the reaction container; detecting the electromagnetic waves that vary according to the state in the reaction container; and controlling transition timing between steps of the plurality of steps based on the detection result of the electromagnetic waves.

Various embodiments will be described hereinafter with reference to the accompanying drawings.

First Embodiment

Figure 1:
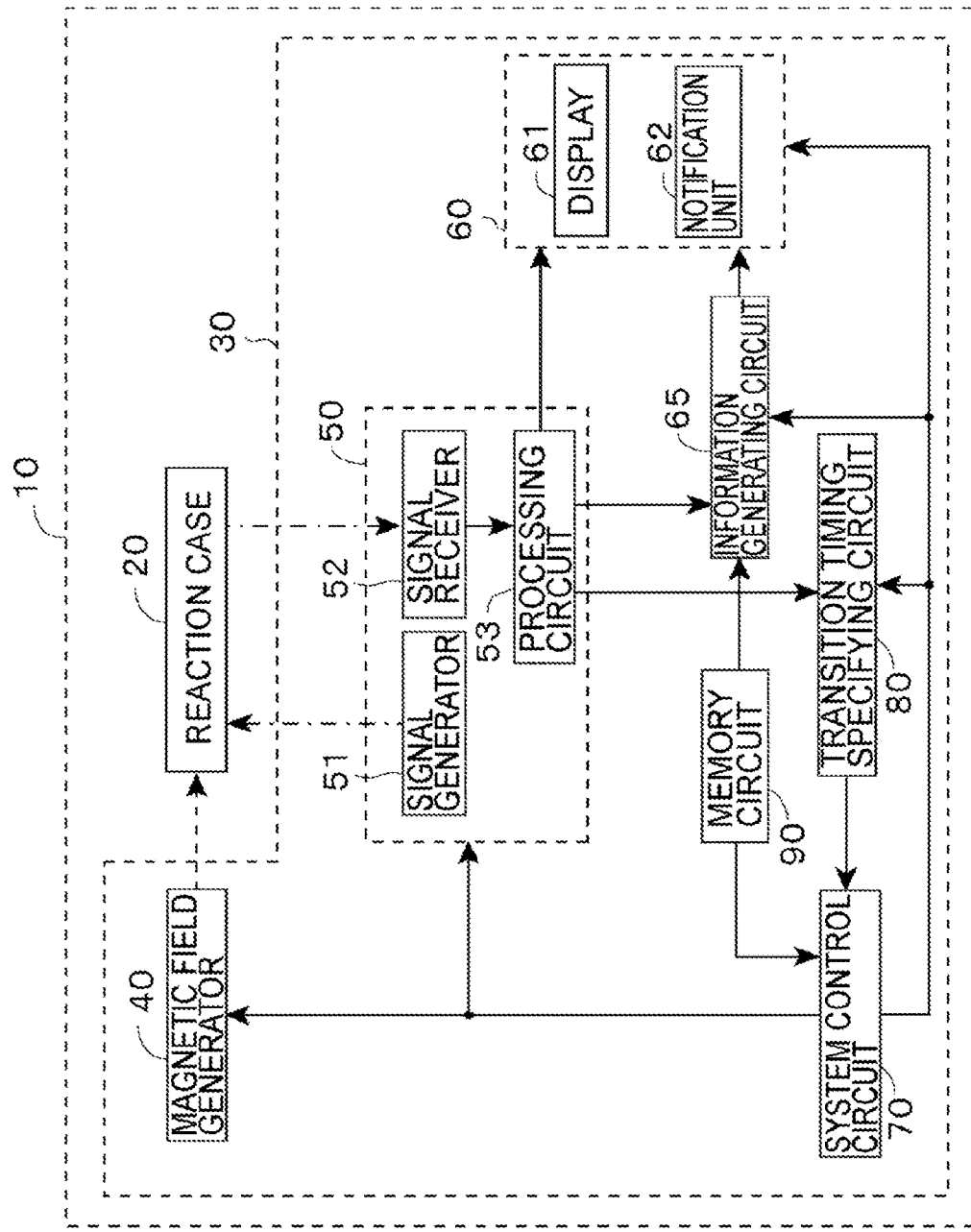
FIG. 1 is a block diagram of an example of the entire configuration of a specimen measurement apparatus according to a first embodiment.
Figure 2:
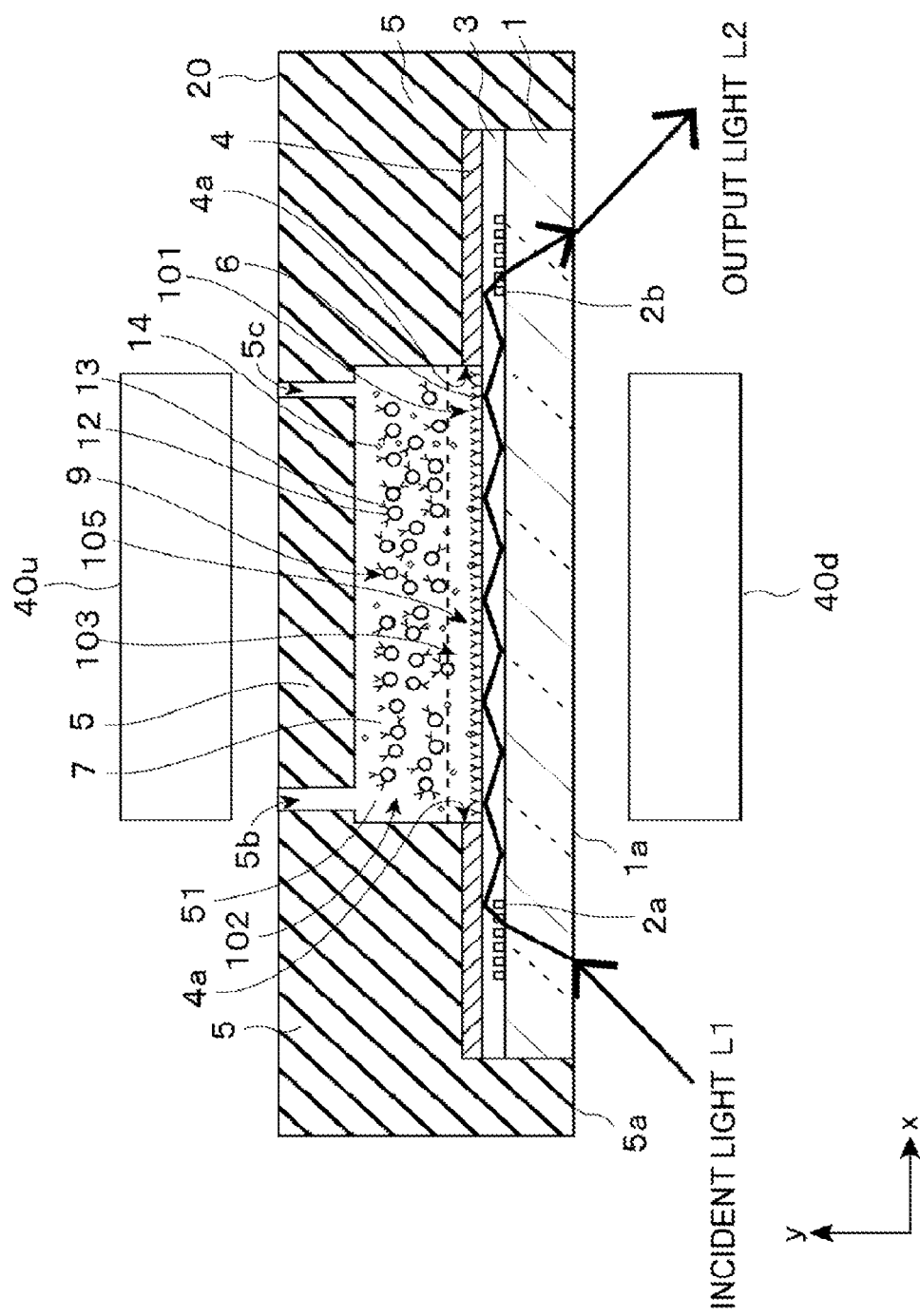
FIG. 2 is a cross-sectional view of an example of the specimen measurement apparatus of the first embodiment.
Figure 3:
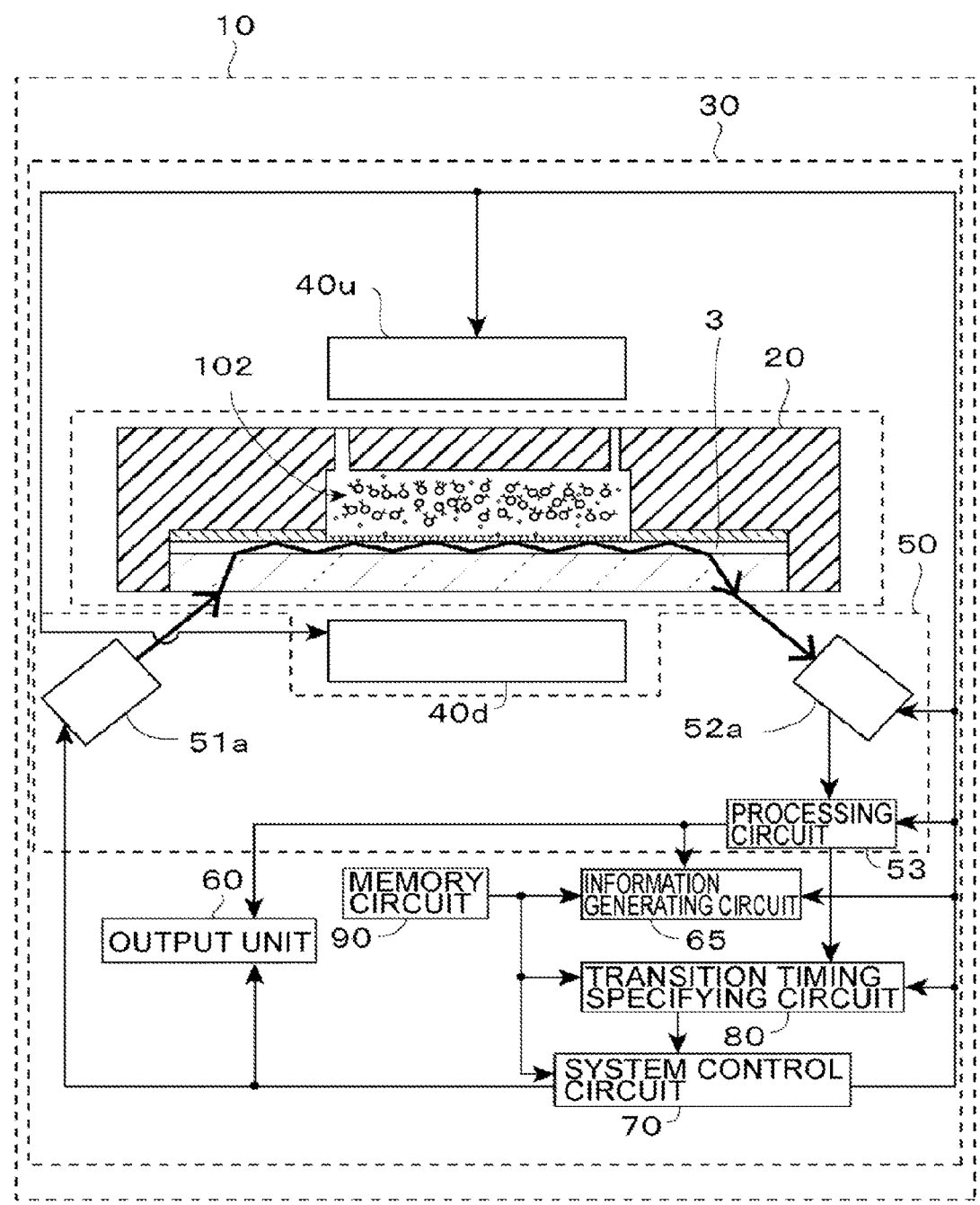
FIG. 3 is a diagram illustrating a detailed structure of a reaction case of the first embodiment.

With reference to FIGS. 1 to 3, a description is given of the configuration of a specimen measurement apparatus 10 according to a first embodiment. FIG. 1 is a block diagram of an example of the entire configuration of the specimen measurement apparatus 10 of the embodiment. As illustrated in FIG. 1, the specimen measurement apparatus 10 includes a reaction case 20 and a measuring instrument 30. The reaction case 20 is attachable to/detachable from the specimen measurement apparatus 10. Described below is the outline of the specimen measurement apparatus 10.

The measuring instrument 30 feeds electromagnetic wave such as light to the reaction case 20 (in the following description, light is used as an example of electromagnetic wave). The light having entered in the reaction case 20 propagates a predetermined region therein, and is affected by the internal conditions of the reaction case 20. Further, the light is output from the reaction case 20 to the measuring instrument 30. The measuring instrument 30 receives the light output from the reaction case 20, and performs predetermined processing on the light signal to obtain a change in the light having been affected by the internal conditions of the reaction case 20. In this embodiment, a plurality of steps is performed along with a series of the above process. The steps include a step of changing the internal conditions of the reaction case 20 which affect the light ("condition change step" described later) and a measurement step. The steps are performed sequentially based on setting information or the like stored in advance.

In this embodiment, according to the result of the predetermined processing by the measuring instrument 30, at least one transition timing is controlled among the steps to reduce the time required for a measurement flow. The transition timing as used herein refers to a timing to complete one step and move to the next step.

(Reaction Case)

The reaction case 20 is configured to retain a sample liquid and a reagent such that a test substance contained in the sample liquid reacts with the reagent therein. As illustrated in FIG. 2, the reaction case 20 includes a casing 5, a transparent substrate 1, an optical waveguide member (optical waveguide) 3, and a protective member 4. Part of the lower surface of the casing 5 forms an opening, in which the transparent substrate 1, the optical waveguide member 3, and the protective member 4 are arranged. The transparent substrate 1 is located at the bottom, and the optical waveguide member 3 is arranged thereon. The protective member 4 is arranged on the optical waveguide member 3, and a part of the protective member 4 forms an opening (opening 4a). The casing 5, the optical waveguide member 3, the protective member 4, and the like define a reaction space 102. The reaction case 20 is configured to be capable of retaining a sample liquid that contains a test object (test substance) in the inside, i.e., in the reaction space 102. In the following, the structure of each part is described. Incidentally, the reaction case 20 is sometimes equated with the casing 5. The reaction case 20 corresponds to an example of "reaction container".

<Casing>

As illustrated in FIG. 2, the upper surface of the casing 5 is provided with a hole 5b for introducing a sample liquid, a reagent, or the like into the reaction space 102 and a hole 5c for releasing pressure from the reaction space 102. Incidentally, there may be a plurality of each of the holes 5b and 5c.

<Optical Waveguide Member>

The optical waveguide member 3 is laminated on the upper surface of the transparent substrate 1. The optical waveguide member 3 propagates light that has entered from the measuring instrument 30 through the transparent substrate 1 and light affected depending on the concentration of a test substance retained in the reaction space 102.

For example, the optical waveguide member 3 is formed as a core layer of a slab optical waveguide (planar optical waveguide). That is, the optical waveguide member 3 is held between the transparent substrate 1 and the protective member 4 using them as cladding, thereby forming a core/cladding structure. Alternatively, the optical waveguide member 3 is held between the transparent substrate 1 and a solution medium 7 that fills the reaction space 102 using them as cladding, thereby forming a core/cladding structure.

<Grating>

A grating 2a deflects the optical path of incident light L1 in the optical waveguide member 3 to enable optical waveguiding. In other words, the grating 2a diffracts light incident on the optical waveguide member 3 at a predetermined angle. The light incident on the grating 2a is diffracted to deflect the optical path, and thus is incident on the interface between the optical waveguide member 3 as a core layer and surfaces that form a cladding (a surface formed of the transparent substrate 1 and the protective member 4 or the solution medium 7) at an angle less than the supplementary angle of the critical angle. Thus, the incident light can be propagated through the optical waveguide member 3.

A grating 2b deflects the optical path of light wave-guided by the optical waveguide member 3 so that the light can be output to the outside. That is, light incident on the optical waveguide member 3 through the grating 2a is totally reflected a plurality of times in the optical waveguide member 3 and then incident on the grating 2b. Having been incident on the grating 2b, the light is diffracted by the grating 2b and thereby the optical path is deflected. Thus, the light is emitted at a predetermined angle from the optical waveguide member 3 to the outside.

<Protective Member>

The protective member 4 is laminated on the transparent substrate 1 to sandwich the optical waveguide member 3 between the protective member 4 and the transparent substrate 1. As laminated on the optical waveguide member 3, the protective member 4 forms a plane protective layer. As illustrated in FIG. 2, the protective member 4 has an opening to expose the main surface (e.g., upper surface) of the optical waveguide member 3. In the following, the inside vertical surfaces of the protective member 4 which define the opening are referred to as "opening 4a". The main surface exposed by the opening 4a corresponds to a sensing surface 101 (described later). Light incident on a surface of the protective member 4 in contact with the optical waveguide member 3 is totally reflected by the surface.

The casing 5 is formed to surround the opening 4a. The reaction space 102 described next is formed as the opening 4a is surrounded by the casing 5.

<Reaction Space>

The reaction space 102 is a space (inner space) for retaining a sample liquid and a reagent such that a test substance contained in the sample liquid reacts with the reagent. A functional layer 105 formed of a plurality of first antibodies 6 (described later) is arranged as the bottom surface among surfaces that define the reaction space 102. The functional layer 105 is laminated to form the sensing surface 101.

The reaction space 102 is, for example, vacant in advance. Upon measurement by the specimen measurement apparatus 10, for example, a sample liquid that contains the solution medium 7 and an antigen 14 as well as a reagent that contains the solution medium 7 and solid dispersion elements 9 are injected in the reaction space 102 through the hole 5b from the outside. With this, the reaction space 102 retains the antigen 14 and second antibodies 13 that constitute part of the solid dispersion elements 9 in addition to the first antibodies 6 that constitute the functional layer 105.

In the reaction case 20, the reaction between the functional layer 105 and a test substance affects light wave-guided in the optical waveguide member 3. The light is output from the optical waveguide member 3 through the transparent substrate 1. As an example of the effect, the incident light L1 (sometimes referred to as "incident light") is attenuated depending on the amount of the antigen 14 retained in the reaction space 102. An example of a configuration for the reaction between the functional layer 105 and a test substance is given in the following description of a sensing area 103.

<<Sensing Area>>

The sensing area 103 is an area where near-field light (evanescent light) can be generated when light propagates through the optical waveguide member 3. Specifically, the sensing area 103 is an area from the surface of the optical waveguide member 3 to the vicinity of the surface of the reaction space 102. As described above, the first antibodies 6 are fixed to the sensing surface 101 in the optical waveguide member 3. The first antibodies 6 are bonded to the second antibodies 13 via the antigen 14, and thereby the sensing surface 101 is bonded to the solid dispersion elements 9 via the antigen 14. Thus, the solid dispersion elements 9 are held in the vicinity of the sensing surface 101.

While light is propagating through the optical waveguide member 3, near-field light is generated on the surface of the optical waveguide member 3. In other words, near-field light is generated in a portion of the sensing surface 101 where the light propagating through the optical waveguide member 3 is totally reflected. The reaction space 102 communicates with the outside via the hole 5c. When a sample liquid or the like is supplied to the reaction space 102, the air in the reaction space 102 is discharged from the hole 5c to the outside.

(Antibodies, Magnetic Microparticles, Etc.)

The antigen 14 and the first antibodies 6, and also the antigen 14 and the second antibodies 13 specifically bind together by antibody-antigen reaction. Through the antibody-antigen reaction, the first antibodies 6 bind to the second antibodies 13 via the antigen 14. Incidentally, while the first antibodies 6, the second antibodies 13, and the antigen 14 are minute with respect to magnetic microparticles 12, they may be illustrated in the same size to schematically indicate the binding reaction between the antigen 14 and the first and second antibodies 6 and 13 (in FIGS. 2, 3, 5A, 5B, 5C, 6A, 6B, 6C, and 7).

<First Antibodies>

The first antibodies 6 are substances that specifically react with the antigen 14 due to antibody-antigen reaction. The sensing surface 101 and the first antibodies 6 are fixed by, for example, hydrophobic interaction, chemical bond, or the like between them. When the antigen 14 is a test substance, the first antibodies 6 specifically bind to the test substance. Those that specifically bind to the test substance may sometimes be referred to as first substances or second substances. In this case, the first antibodies 6 correspond to the first substances.

<Solid Dispersion Elements>

The solid dispersion elements 9 include carriers which carry the second antibodies 13. The second antibodies 13 that constitute part of the solid dispersion elements 9 bind to the first antibodies 6 via the antigen 14, and thereby the solid dispersion elements 9 are fixed in the vicinity of the sensing surface 101. At this time, if near-field light is generated on the sensing surface 101, the carriers that constitute part of the solid dispersion elements 9 disperse and/or absorb the light.

While the carriers may be of any type as long as they can be dispersed in the solution medium 7, typically, solid particles are selected as the carriers. In this embodiment, the magnetic microparticles 12 (described later) having magnetic properties are used as the carriers.

When the reaction space 102 is filled with the solution medium 7 and the solid dispersion elements 9 are introduced into the solution medium 7, the solid dispersion elements 9 move as being dispersible in the solution medium 7. The solution medium 7 and the solid dispersion elements 9 are selected such that the gravity on the solid dispersion elements 9 at this time is larger than the sum of the buoyancy applied thereto in the reverse direction to the gravity and the resistance from the solution medium 7. The solution medium 7 is made of a liquid.

The dispersion, absorption, and the like of the near-field light in the sensing area 103 affect the light that propagates through the optical waveguide member 3. When the solid dispersion elements 9 enter the sensing area 103, the near-field light is scattered or absorbed by the solid dispersion elements 9. The near-field light attenuates due to the dispersion or absorption. The attenuation of the near-field light also affects the light that is wave-guided through the optical waveguide member 3. That is, if the near-field light attenuates, the light that is wave-guided through the optical waveguide member 3 also attenuates accordingly. In other words, if the near-field light is dispersed and absorbed strongly in the sensing area 103, this reduces the intensity of the light that propagates through the optical waveguide member 3. This means that as the amount of the solid dispersion elements 9 increases in the sensing area 103, the intensity of light output from the optical waveguide member 3 decreases. Here, the light that is wave-guided through the optical waveguide member 3 refers to the light that propagates (is wave-guided) while being repeatedly reflected on the interface of the optical waveguide member 3.

In this manner, the reaction case 20 includes the sensing surface 101, and retains the solid dispersion elements 9 and the antigen 14 in the reaction space 102 which is in contact with the sensing surface 101. That is, the sensing surface 101 is one of surfaces that define the reaction space 102. With this, near-field light generated in the sensing surface 101 attenuates, resulting in a change in the intensity of light output from the reaction case 20.

<<Magnetic Microparticles>>

The magnetic microparticles 12 are at least partly formed of magnetic material. For example, the magnetic microparticles 12 are formed by coating the surface of particles made of magnetic material with polymer material. The magnetic microparticles 12 may also be formed by coating the surface of particles made of polymer material with magnetic material.

<<Second Antibodies>>

The second antibodies 13 are substances that specifically react with the antigen 14. The second antibodies 13 correspond to the second substances. The second antibodies 13 are fixed to the surfaces of the magnetic microparticles 12. The second antibodies 13 may be the same as or different from the first antibodies 6. The first antibodies 6 and the second antibodies 13 may sometimes be correctively referred to as "antibodies".

When the functional layer 105 binds to the solid dispersion elements 9 via the antigen 14, the solid dispersion elements 9 stay in the sensing area 103. At this time, if light is being wave-guided through the optical waveguide member 3, near-field light generated in the sensing area 103 is dispersed or absorbed. As a result, the intensity of the light that is wave-guided through the optical waveguide member 3 is attenuated.

Incidentally, not all the solid dispersion elements 9 that stay in the sensing area 103 are those specifically binding to the functional layer 105 via the antigen 14 to be measured. Therefore, the solid dispersion elements 9 not related to the measurement are required to be separated from the sensing area 103. For example, the solid dispersion elements 9 may be moved by action through a medium due to the magnetic field. In this case, the solid dispersion elements 9 contain the magnetic microparticles 12.

Thus, the specimen measurement apparatus 10 can measure the amount, concentration, and the like of the antigen 14 retained in the reaction space 102 based on the intensity of the light and a time-series variation in the intensity. That is, the reaction case 20 is configured such that light that propagates through the optical waveguide member 3 is attenuated according to the internal environment of the reaction space 102. The internal environment of the reaction space 102 may be indicated by a variety of parameters. Examples of the parameters for the internal environment include the concentration of the antigen 14. In other words, the concentration of the antigen 14 as a parameter for the internal environment determines the degree of the attenuation of light that propagates through the optical waveguide member 3.

(Measuring Instrument)

The measuring instrument 30 includes a detector 50, a magnetic field generator 40, an output unit 60, an information generating circuit 65, a system control circuit 70, an operation circuit (not illustrated), a transition timing specifying circuit 80, and a memory circuit 90.

<Detector>

As illustrated in FIG. 1, the detector 50 includes a signal generator 51, a signal receiver 52, and a processing circuit 53. The signal generator 51 outputs a signal to the reaction case 20. The signal receiver 52 receives a signal output from the reaction case 20, and outputs information of the signal to the processing circuit 53. This series of processes may sometimes be referred to as "detection process". The processing circuit 53 processes the information of the signal and thereby generates, for example, time-series variation information for the signal. The signal may be, for example, light, electromagnetic wave, sound, or the like. In the following, the signal is described as light with reference to FIG. 3.

FIG. 3 is a diagram illustrating an example of the specimen measurement apparatus of the embodiment. As illustrated in FIG. 3, the detector 50 includes a light source 51a, a light receiving device 52a, and the processing circuit 53. The light source 51a is an example of the signal generator 51. The light receiving device 52a is an example of the signal receiver 52. The light source 51a emits light to be incident on the optical waveguide member 3 of the reaction case 20 such that the light is wave-guided therethrough. The light receiving device 52a receives the light that has been wave-guided through the optical waveguide member 3 and then output therefrom.

<<Light Source>>

The light source 51a generates light to be incident on the reaction case 20. The light generated by the light source 51a is output to the reaction case 20. The output light is incident on a predetermined position of the grating 2a at the entrance as incident light L1. The light that has entered the optical waveguide member 3 from the light source 51a is diffracted by the grating 2a on the entrance side and wave-guided through the optical waveguide member 3.

The light output from the light source 51a is, for example, light beams such as laser beams. The light may be continuous light with an intensity that substantially does not vary in the time series. When the light source 51a emits light beams, the beam width is made narrower than the width of the optical waveguide member 3 so that every single beam of light emitted from the light source 51a can enter the optical waveguide member 3. Thus, the intensity of light emitted from the light source 51a can be regarded as that of the incident light L1 on the optical waveguide member 3. Examples of the light source 51a include, for example, light emitting diodes (LEDs), laser diodes (LDs), and the like.

<<Light Receiving Device>>

As illustrated in FIG. 3, the light receiving device 52a performs the detection process of receiving light incident from the outside. The light receiving device 52a is arranged at a position where it can receive output light L2 emitted toward the outside from the grating 2b at the exit. The light receiving device 52a includes, for example, a light receiving element (photosensor) such as a photodiode. The light receiving element is arranged at a position where it can receive light emitted through the grating 2b. When the light source 51a emits laser beams, the light receiving device 52a includes, as the light receiving element, the one having a width (size) larger than the beam width of light output from the optical waveguide member 3. By using such a light receiving element, every single beam of light output from the optical waveguide member 3 can be received. Thus, the intensity of light received by the light receiving device 52a can be regarded as that of light output from the optical waveguide member 3, i.e., the intensity of the output light L2. The light receiving device 52a feeds the processing circuit 53 with information of the output light L2 received thereon. That is, having received the incident light L1 from the light source 51a, the reaction case 20 performs sensing in the sensing area 103, and outputs light that includes sensing information as the output light L2 to the light receiving device 52a.

<<Processing Circuit>>

Having received the information of the output light L2 from the light receiving device 52a, the processing circuit 53 performs processing on the information. Through the processing, the processing circuit 53 can acquire such information as, for example, the intensity, wavelength, phase and the like of the output light L2. For example, the processing circuit 53 performs processing on the information of the light with time to obtain time-series information of the output light L2. As one example, the processing circuit 53 uses the intensity of the output light L2 as an output signal. In this case, the processing circuit 53 processes the intensity of the output light L2 with time, and thereby obtains time-series information of the intensity of the output light L2. The processing circuit 53 continuously obtains the intensity of the output light L2. Alternatively, the processing circuit 53 may obtain the intensity of the output light L2 at regular intervals.

Besides, the processing circuit 53 may generate information that indicates relationship with respect to the initial value of an output signal from the reaction case 20. As one example, the processing circuit 53 uses the intensity of the output light L2 as an output signal. In this case, the processing circuit 53 obtains a light intensity ratio based on the intensity of the output light L2. The light intensity ratio refers to the ratio of the light intensity based on the initial value of the intensity of the output light L2. The light intensity ratio is obtained by dividing the value of the output light L2 acquired by the initial value of the output light L2. The processing circuit 53 processes the light intensity ratio with time, and thereby obtains time-series information of the light intensity ratio.

Further, the processing circuit 53 may generate information that indicates relationship between an input signal to the reaction case 20 and an output signal from the reaction case 20. As one example, the processing circuit 53 uses the relationship between an input signal and an output signal as an input/output light intensity ratio between the intensity of the incident light L1 and that of the output light L2. In this case, the processing circuit 53 obtains, for example, the intensity of light output from the light source 51a to the reaction case 20 as information of the incident light L1 on the reaction case 20 in addition to the information of the output light L2 received from the light receiving device 52a. The relationship between an input signal and an output signal may be a wavelength ratio between the incident light L1 and the output light L2.

The processing circuit 53 sequentially outputs the time-series information thus obtained to the transition timing specifying circuit 80. The time-series information may be selected from those described above as appropriate; however, it is preferably the time-series information of light intensity or light intensity ratio. The transition timing specifying circuit 80 specifies step-to-step transition timing based on the time-series information received from the processing circuit 53. The transition timing specifying circuit 80 is described in detail later. The detection process may include the process performed by the processing circuit 53.

A variety of information generated by the processing circuit 53 may be output to the output unit 60. The processing circuit 53 outputs, for example, information indicating a change in the properties of output light L2. A graph creating circuit (not illustrated) is provided as an example of the processing circuit 53.

The graph creating circuit is capable of creating a graph as the information indicating a change in the properties of output light L2. This graph illustrates, as a change in the properties, for example, a time-series variation in the light intensity. In this graph, the inclination of a curve represents the change rate of the intensity of the output light L2. Alternatively, for example, the graph illustrates an intensity ratio with respect to the intensity of the output light L2 immediately after the start of measurement in time series. The intensity ratio is the one at a certain time based on the light intensity immediately after the start of measurement. In this graph, the inclination of a curve represents the change rate of the intensity ratio. The graph is output to a display 61 to be displayed on the display screen. The display of the graph enables the operator to visually check a time-series variation in the intensity of the output light L2.

The graph creating circuit may create a graph that illustrates a change in comparison information obtained by a comparison between the properties of the incident light L1 and those of the output light L2. The change in the comparison information corresponds to a time-series variation in the intensity ratio between the incident light L1 and the output light L2. The graph created illustrates, for example, the intensity ratio between the incident light L1 and the output light L2 in time series. In this graph, the inclination of a curve represents the change rate of the intensity ratio. While the graph creating circuit is configured to be capable of creating different types of graphs as described above, it suffices if it can create at least a graph that illustrates a time-series variation in the intensity of the output light L2.

<Magnetic Field Generator>

The magnetic field generator 40 includes an upper magnetic field applicator 40u and a lower magnetic field applicator 40d. The magnetic field generator 40 further includes a drive circuit (not illustrated). Under the control of the system control circuit 70, the drive circuit drives the magnetic field generator 40 to apply a magnetic field to the reaction space 102. Thereby, the magnetic field generator 40 generates a magnetic force with respect to the solid dispersion elements 9 (the magnetic microparticles 12) retained in the reaction space 102. That is, the magnetic field generator 40 generates a magnetic flux vertically penetrating through the reaction space 102. The magnetic field generator 40 may be formed of, for example, a permanent magnet, an electromagnet, or a combination of them. For example, the magnetic field generator 40 includes the upper magnetic field applicator 40u capable of generating an upward magnetic flux that vertically penetrates through the reaction space 102 and the lower magnetic field applicator 40d capable of generating a downward magnetic flux that vertically penetrates through the reaction space 102.

The upper magnetic field applicator 40u and the lower magnetic field applicator 40d apply a magnetic field to the reaction space 102. As described above, the solid dispersion elements 9 include the magnetic microparticles 12. The magnetic field applied to the reaction space 102 generates a force in the solid dispersion elements 9 retained in the reaction space 102. The movement of the solid dispersion elements 9 can be controlled by controlling the force. For example, the application of an upward magnetic field to the reaction space 102 can separate the solid dispersion elements 9 not related to an object to be measured (not related to the antigen 14) from the sensing area 103.

As an example of the magnetic field generator 40, the detailed configuration of the upper magnetic field applicator 40u is described with reference to FIGS. 2 and 3.

<<Upper Magnetic Field Applicator>>

As illustrated in FIGS. 2 and 3, the upper magnetic field applicator 40u is located above the reaction case 20. The upper magnetic field applicator 40u generates a magnetic field in the vertically upward direction (hereinafter sometimes referred to as "upper magnetic field") uniformly in the horizontal direction. Due to the magnetic field, a vertically upward force is applied to the solid dispersion elements 9 (the magnetic microparticles 12) retained in the reaction space 102. The solid dispersion elements 9 are moved vertically upward by this force. In this case, by setting the force applied to the solid dispersion elements 9 to be smaller than the binding force between the first antibodies 6 and the antigen 14 as well as that between the second antibodies 13 and the antigen 14, the solid dispersion elements 9 that provide an error factor can be selectively separated from the sensing area 103. In other words, when the upward force is applied to the solid dispersion elements 9 due to the upper magnetic field, the solid dispersion elements 9 not related to measurement are selectively separated from the sensing area 103. This application of the upper magnetic field is conducted to keep the solid dispersion elements 9 related to measurement staying in the sensing area 103.

For example, if the upper magnetic field applicator 40u is formed of a permanent magnet, the permanent magnet is arranged such that one end thereof, which is a pole of the magnet, faces the surface of the optical waveguide member 3 that forms the reaction space 102. Besides, the upper magnetic field applicator 40u may be formed of a plurality of permanent magnets arranged in parallel with their poles directed to the same direction. In this case, the intensity of a magnetic field applied to the reaction space 102 can be adjusted by the intensity of the permanent magnet(s), distance from the reaction space 102, and the like. The intensity of the magnetic field may also be adjusted by arranging a spacer between the permanent magnet(s) and the reaction space 102 and changing the thickness of the spacer. If the spacer is configured to be capable of completely shutting off the magnetic field, the intensity of the magnetic field applied to the reaction space 102 can be made zero. Further, with the use of an actuator such as a linear motor, the adjustment can be achieved by changing the relative positions of the permanent magnet(s) and the reaction space 102.

If the upper magnetic field applicator 40u is formed of an electromagnet, the coil is arranged such that one end thereof faces the surface of the optical waveguide member 3 that forms the reaction space 102. In this case, the intensity of a magnetic field applied to the reaction space 102 can be adjusted by the size of an electric current applied to the electromagnet, distance from the reaction space 102, and the like. If the intensity of a magnetic field applied to the reaction space 102 is zero, the electric current applied to the electromagnet is zero.

The magnetic flux that penetrates through the reaction space 102 may sometimes be horizontally spread out toward the vertically downward direction. However, if the spread is ignored, the magnetic flux can be regarded as vertically penetrating through the reaction space 102. The spread is ignorable because the distance between the surface of the optical waveguide member 3 that forms the reaction space 102 and the pole of the upper magnetic field applicator 40u that faces the surface is very small.

<<Lower Magnetic Field Applicator>>

The lower magnetic field applicator 40d is located below the reaction case 20. The lower magnetic field applicator 40d generates a magnetic field in the vertically downward direction (hereinafter sometimes referred to as "lower magnetic field") uniformly in the horizontal direction. Due to the magnetic field, for example, a plurality of vertically downward magnetic fluxes are generated at regular intervals. The magnetic fluxes penetrate through the reaction space 102 in the vertically downward direction from the surface to the bottom. By reversing the direction of a magnetic field to be generated, the lower magnetic field applicator 40d may serve as the upper magnetic field applicator 40u.

The lower magnetic field applicator 40d may be located opposite the upper magnetic field applicator 40u across the reaction case 20. In this case, the upper magnetic field applicator 40u and the lower magnetic field applicator 40d are formed of electromagnets. In addition, different poles of the upper magnetic field applicator 40u and the lower magnetic field applicator 40d face the reaction case 20. This can reduce the above-mentioned spread of the magnetic flux in the horizontal direction. For example, the north pole of the upper magnetic field applicator 40u faces the reaction case 20, while the south pole of the lower magnetic field applicator 40d faces the reaction case 20. Thereby, it is possible to stably generate magnetic fluxes that penetrate through the reaction space 102 in the vertically upward direction.

<Information Generating Circuit>

The information generating circuit 65 generates information indicating measurement results based on processing results obtained by the processing circuit 53. Examples of the processing results include the value of the intensity of the output light L2 and the value of a light intensity ratio. Examples of the measurement results include the amount of the antigen 14. The amount of the antigen 14 refers to the number, concentration, weight or the like of the antigen 14. The generation of the information indicating measurement results is described in detail in the explanation of the measurement process performed by the system control circuit 70.

<System Control Circuit>

The system control circuit 70 is configured to control each of the detector 50, the output unit 60, and the transition timing specifying circuit 80. The operation circuit (not illustrated) is operated to provide the system control circuit 70 with a variety of inputs.

The system control circuit 70 controls the specimen measurement apparatus 10 based on setting information stored in the memory circuit 90 in advance. Specifically, based on a plurality of steps of a measurement flow indicated by the setting information, the system control circuit 70 sequentially controls the constituent elements related to the steps. Described below is an example of the measurement flow. In this measurement flow, three preparation steps are performed before the step of performing final measurement (measurement step). These preparation steps are referred to as first, second, and third state change steps in the order of time series.

As described above, from the start of measurement until measurement results are obtained, processing on a signal (light or electromagnetic wave) output from the light receiving device 52a is performed continuously as well as in parallel. The measurement flow described below illustrates a typical example of a case where the control of this embodiment is not applied. The measurement flow is provided for a comparison with the process (described later) accompanied by the control of this embodiment.

The measurement flow is started in response to a trigger indicating that the reaction case 20 is mounted on the specimen measurement apparatus 10, and the introduction of a test liquid into the reaction space 102 is completed. Specifically, the measuring instrument 30 starts projecting/receiving light for signal data collection by the detector 50. A contact sensor (not illustrated) is provided on a surface of the specimen measurement apparatus 10, where the reaction case 20 is placed, to detect that the reaction case 20 is mounted on the specimen measurement apparatus 10. Besides, after the reaction case 20 is mounted on the specimen measurement apparatus 10, the measuring instrument 30 projects/receives light to/from the detector 50 to detect the introduction of a test liquid into the reaction space 102 by a change in the signal. That is, the receiving light intensity changes in projecting/receiving light when a test liquid is introduced into the reaction space 102, and thus the introduction can be detected.

The system control circuit 70 starts controlling the lower magnetic field applicator 40d based on the setting information. In response to the start of the control, the lower magnetic field applicator 40d generates a magnetic field directed downward (lower magnetic field) in the reaction space 102. Because the solid dispersion elements 9 include the magnetic microparticles 12, a downward magnetic force is applied thereto due to the lower magnetic field. While, in this embodiment, the lower magnetic field applicator 40d continuously generates lower magnetic fields of substantially the same intensity, this is not so limited in other embodiments.

After the lapse of a predetermined time from the start of the generation of the lower magnetic field indicated by the setting information, the system control circuit 70 sends an instruction to stop generating the lower magnetic field to the lower magnetic field applicator 40d. With this, the lower magnetic field applied to the reaction space 102 disappears, and thus the solid dispersion elements 9 are no longer bound by the magnetic field. This step from the start to the stop of the application of the lower magnetic field may sometimes be referred to as "lower magnetic field application step". The lower magnetic field application step is an example of the first state change step.

As being free from the restraining influence of the lower magnetic field, the solid dispersion elements 9 start spontaneously precipitating to the sensing surface 101. After a predetermined period of the spontaneous precipitation, the solid dispersion elements 9 are accumulated in the vicinity of the sensing surface 101. The system control circuit 70 specifies the timing for the end of the spontaneous precipitation based on the setting information. This step from the stop of the application of the lower magnetic field to the end of the spontaneous precipitation may sometimes be referred to as "spontaneous precipitation step". The spontaneous precipitation step is an example of the second state change step.

The timing for the end of the spontaneous precipitation step corresponds to the timing for the start of the next step (the third state change step) indicated by the setting information. Upon arrival of the timing for the end of the spontaneous precipitation step, the system control circuit 70 starts driving the upper magnetic field applicator 40u. According to the control, the upper magnetic field applicator 40u generates a magnetic field directed upward (upper magnetic field) in the reaction space 102. Due to the upper magnetic field, an upward magnetic force is applied to the solid dispersion elements 9. This step after the start of the application of the upper magnetic field may sometimes be referred to as "upper magnetic field application step". The upper magnetic field application step is an example of the third state change step. In this embodiment, similarly to the lower magnetic field, the intensity of the upper magnetic field is substantially unchanged.

After the lapse of a predetermined time from the start of the application of the upper magnetic field indicated by the setting information, the system control circuit 70 sends processing results obtained by the processing circuit 53 at this timing to the information generating circuit 65. This process may be performed in such a manner that the system control circuit 70 forwards the processing results from the processing circuit 53 to the information generating circuit 65, or that the processing circuit 53 directly sends the results to the information generating circuit 65 under the control of the system control circuit 70. The information generating circuit 65 generates information indicating measurement results based on the processing results. In this manner, based on the detection results of the output light L2 obtained by the detector 50, the system control circuit 70 performs a control to change at least one of the size of a force applied to the solid dispersion elements 9, a period of time during which the force is acting on the solid dispersion elements 9, and the direction in which the force is applied to the solid dispersion elements 9.

Figure 4:
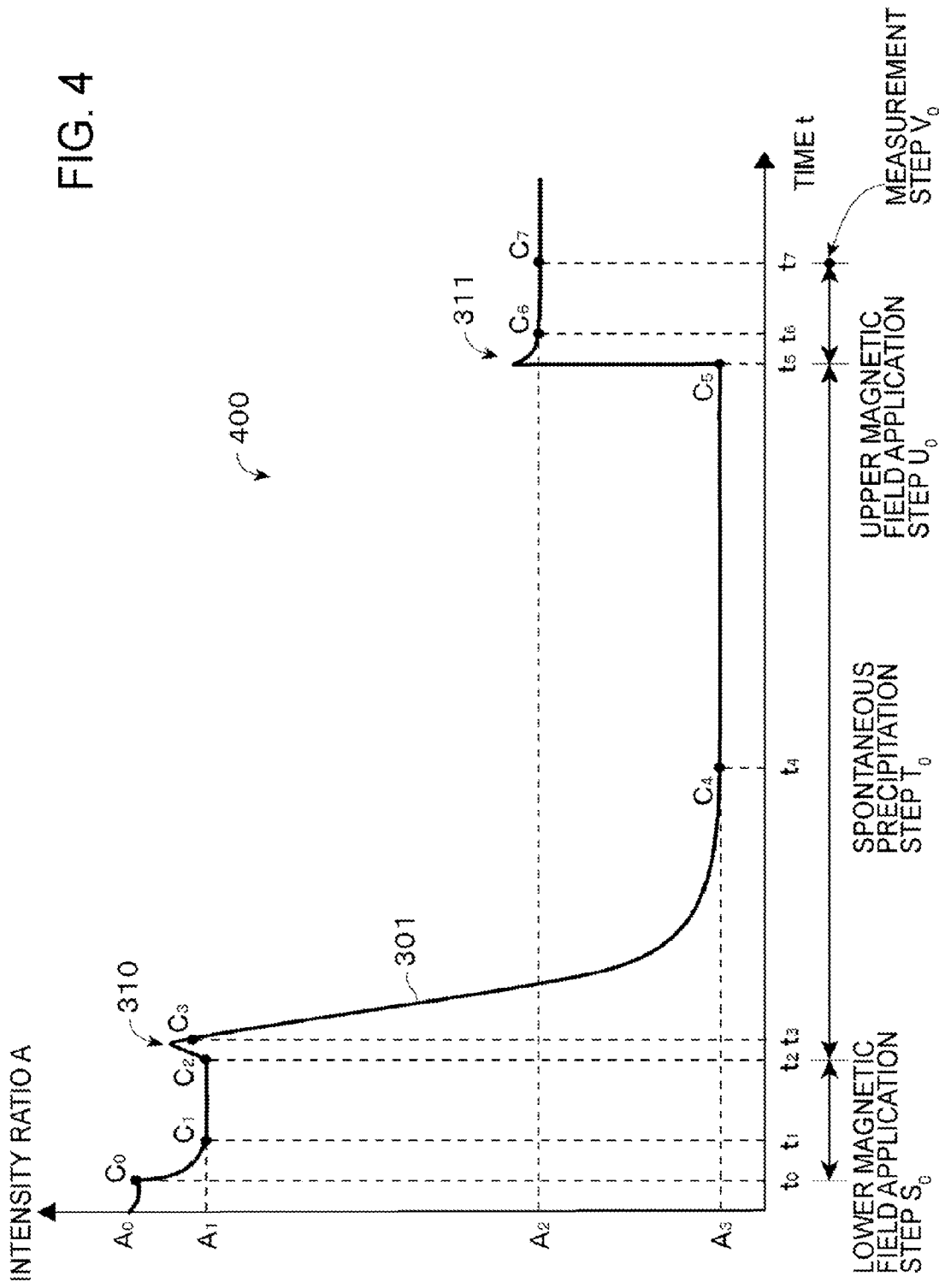
FIG. 4 is a graph illustrating a time-series variation in the intensity ratio of output light.

FIG. 4 is a graph 400 that illustrates a time-series variation in the light intensity sequentially acquired in a predetermined period of time (at regular intervals) by the processing circuit 53. In the graph 400, the horizontal axis indicates time t, while the vertical axis indicates the intensity ratio A of the output light L2. A curve 301 is obtained by plotting temporal changes in the intensity ratio A. Light continuously enters the optical waveguide member 3 from the start of the acquisition of data of the intensity ratio A (t=0) until the time $t_7$ when final measurement is performed. This light is emitted from the light source 51a, and the intensity thereof is substantially unchanged.

The intensity ratio A is a ratio of the light intensity to the intensity of the output light L2 at the time t=0 as a reference. The value of the intensity ratio A varies according to the amount of the solid dispersion elements 9 present in the sensing area 103. That is, more amounts of the solid dispersion elements 9 are present in the sensing area 103 as the intensity ratio A decreases, while less amount of the solid dispersion elements 9 are present as the intensity ratio A increases. FIGS. 2 and 3 are referred to as appropriate in the explanation of FIG. 4. Besides, a sample liquid fed into the reaction case 20 contains the antigen 14.

In a test based on the measurement flow illustrated in FIG. 4, provided the measurement start time is t=0, the lower magnetic field application step $S_0$, the spontaneous precipitation step $T_0$, the upper magnetic field application step $U_0$, and the measurement step $V_0$ are performed in this order. The time t=0 is, for example, the time when the reaction space 102 is filled with the sample liquid. The lower magnetic field application step $S_0$ is performed during a period $t_0$ to $t_2$ ($t_0 \leq t \leq t_2$). The spontaneous precipitation step $T_0$ is performed during a period $t_2$ to $t_5$ ($t_2 \leq t \leq t_5$). The upper magnetic field application step $U_0$ is performed during a period $t_5$ to $t_7$ ($t_5 \leq t \leq t_7$). The measurement step $V_0$ is performed at the time $t=t_7$ as the end time of the upper magnetic field application step $U_0$.

(Lower Magnetic Field Application Step)

Figure 5A:
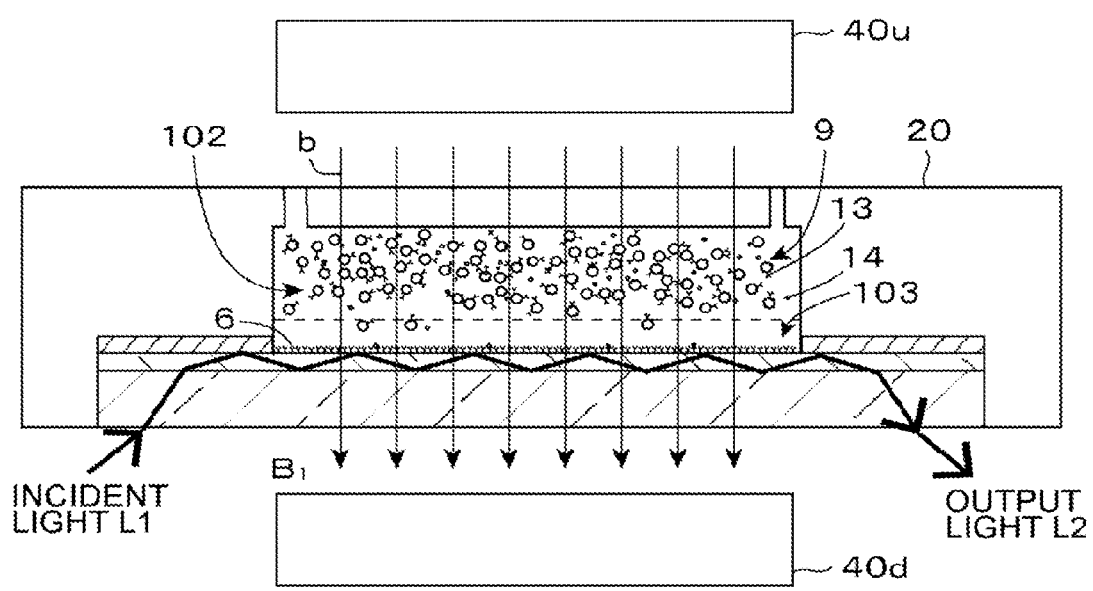
FIG. 5A is a view of a reaction space at a predetermined time.
Figure 5B:
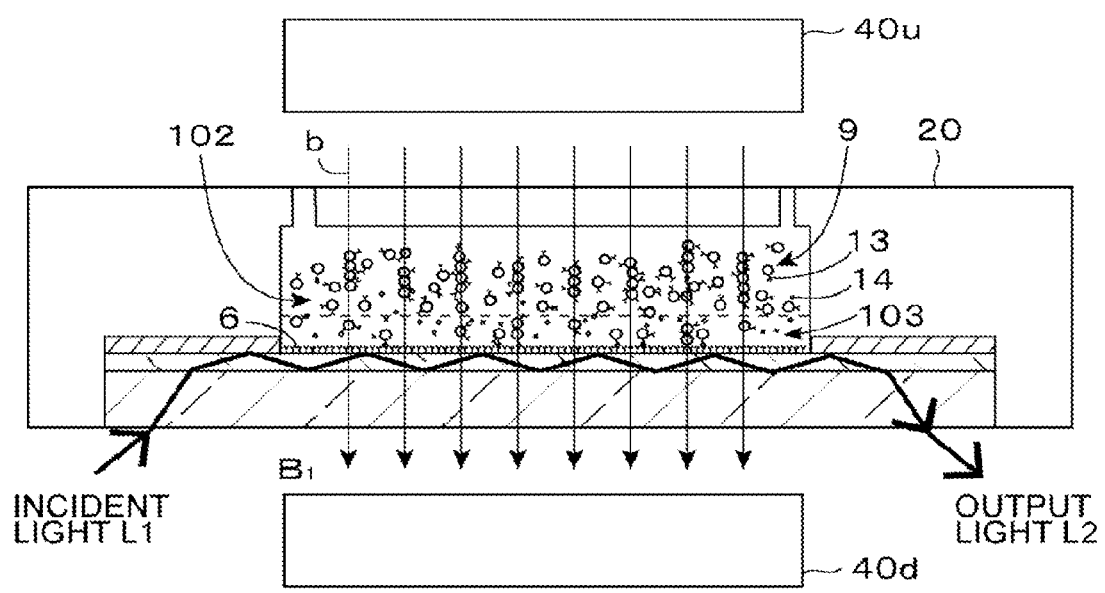
FIG. 5B is a view of the reaction space at a predetermined time.
Figure 5C:
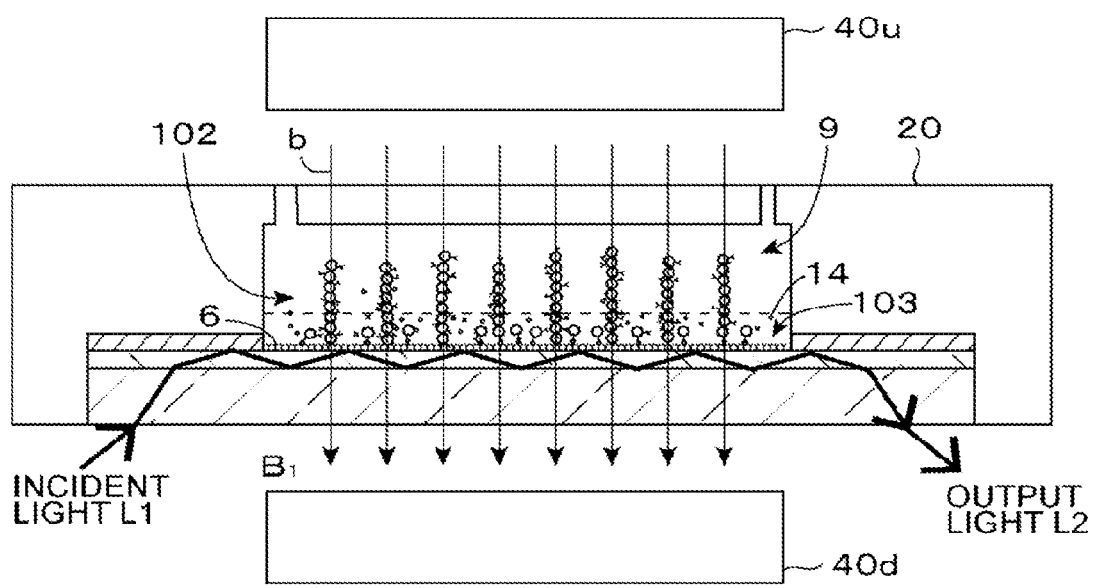
FIG. 5C is a view of the reaction space at a predetermined time.

With reference to FIGS. 5A to 5C, a description is given of the action of the solid dispersion elements 9 in the lower magnetic field application step $S_0$. FIG. 5A is a cross-sectional view illustrating the state in the reaction space 102 at the time $t=t_0$. FIG. 5B is a cross-sectional view illustrating the state in the reaction space 102 at the time $t=\tau_0$ ($t_0 < \tau_1 < t_1$). FIG. 5C is a cross-sectional view illustrating the state in the reaction space 102 at the time $t=\tau_2$ ($t_1 \leq \tau_2 < t_2$).

In the lower magnetic field application step $S_0$, the value of the intensity ratio A converges to a first predetermined value after a decrease phase and a convergence phase. In this step, gravity and downward force are applied to the solid dispersion elements 9 in the environment of the lower magnetic field. The lower magnetic field is applied to the reaction space 102 to shorten the time it takes for the solid dispersion elements 9 reach the sensing area 103.

As illustrated in FIG. 5A, at the time t=0, the reaction space 102 is filled with the sample liquid. Since the downward gravity is applied to the solid dispersion elements 9 contained in the sample liquid, part of the solid dispersion elements 9 precipitates and enters the sensing area 103. At this time, at least part of the antigen 14 contained in the sample liquid binds to the second antibodies 13 and precipitates toward the sensing surface 101. With this, the intensity ratio A measured during a period from the time t=0 to $t=t_0$ decreases a little. At the time $t=t_0$, the application of the lower magnetic field is started. In the figures, downward arrows indicate the direction of a magnetic flux $B_1$ generated due to the application of the lower magnetic field. The magnetic flux $B_1$ is formed of a plurality of magnetic lines b, and substantially penetrates downward through the reaction space 102.

As illustrated in FIG. 5B, part of the solid dispersion elements 9, to which a downward magnetic force is being applied due to the lower magnetic field, is attracted by the magnetic lines b and arrayed along them. The solid dispersion elements 9 arrayed along the magnetic lines b gradually precipitate by gravity and magnetic force, and enter the sensing area 103. Part of the solid dispersion elements 9 that have entered the sensing area 103 bind to the sensing surface 101. On the other hand, the solid dispersion elements 9 not arrayed along the magnetic lines b gradually precipitate by gravity, and bind to the sensing surface 101. In a period $t_0$ to $t_1$ illustrated in FIG. 5B, the solid dispersion elements 9 sequentially enter the sensing area 103, and accordingly, the curve 301 represents the decrease phase at the initial stage (section $C_0$ to $C_1$). In the decrease phase, the intensity ratio A starts decreasing at high rate (large inclination) from the point immediately after the time $t=t_0$. The decrease rate is maintained for a predetermined period of time and gradually lowers. At the time $t=t_1$, the decrease rate of the intensity ratio A is almost zero. At the time $t=t_1$ the state that the solid dispersion elements 9 enter the sensing area 103 is substantially steady, and the curve 301 represents the convergence phase. That is, during a period $t_1$ to $t_2$, the intensity ratio A converges to $A_1$ (the intensity ratio $A=A_1$) as the first predetermined value (section $C_0$ to $C_1$). FIG. 5C illustrates an example of the inside of the reaction space 102 in this state. In this phase also, at least part of the antigen 14 contained in the sample liquid sequentially binds to the second antibodies 13.

(Spontaneous Precipitation Step)

Figure 6A:
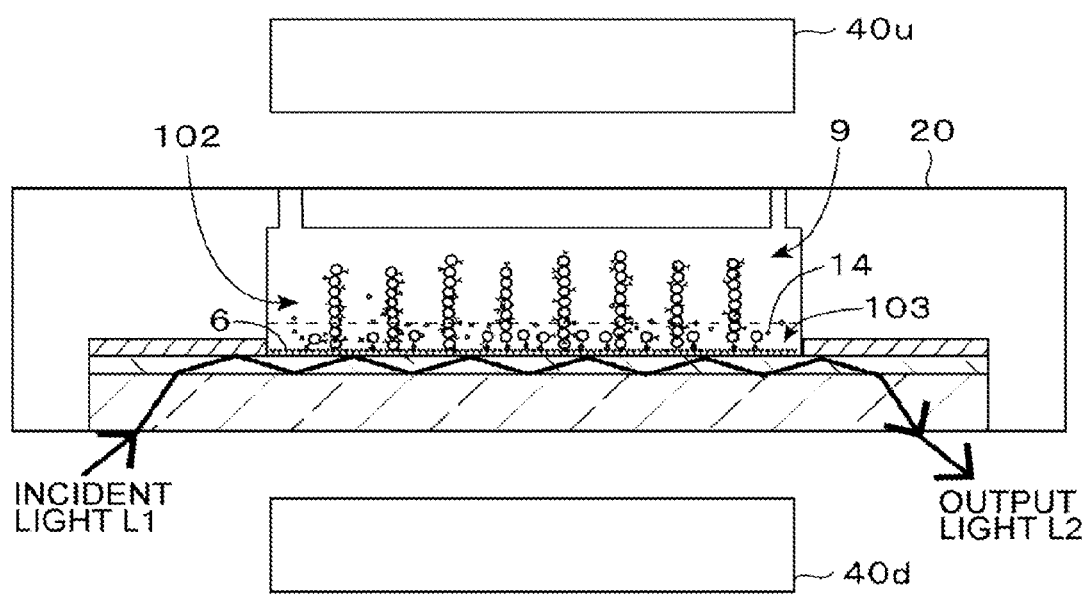
FIG. 6A is a view of the reaction space at a predetermined time.
Figure 6B:
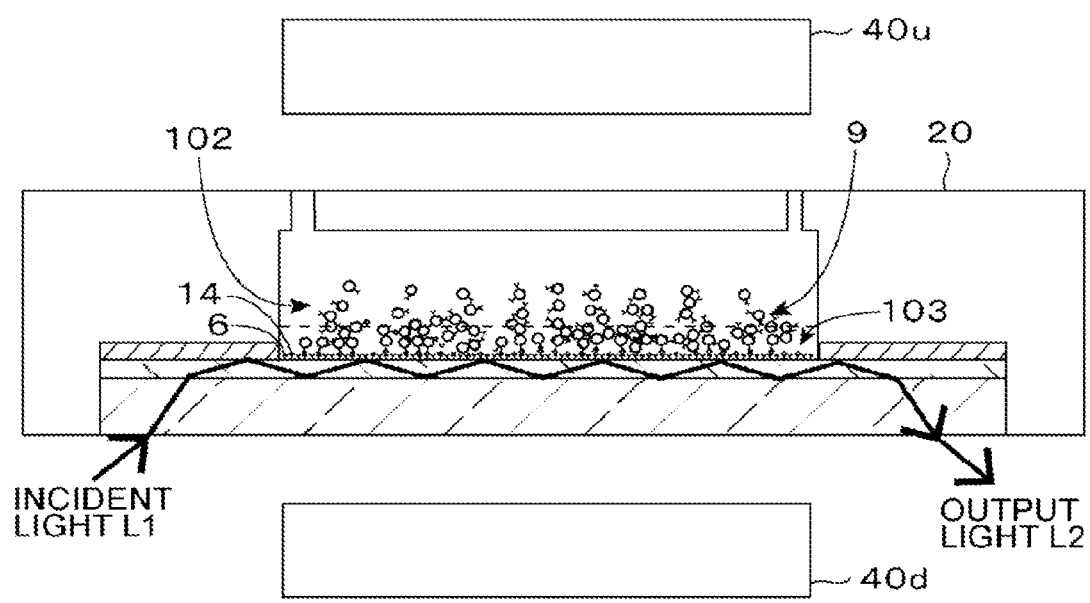
FIG. 6B is a view of the reaction space at a predetermined time.
Figure 6C:
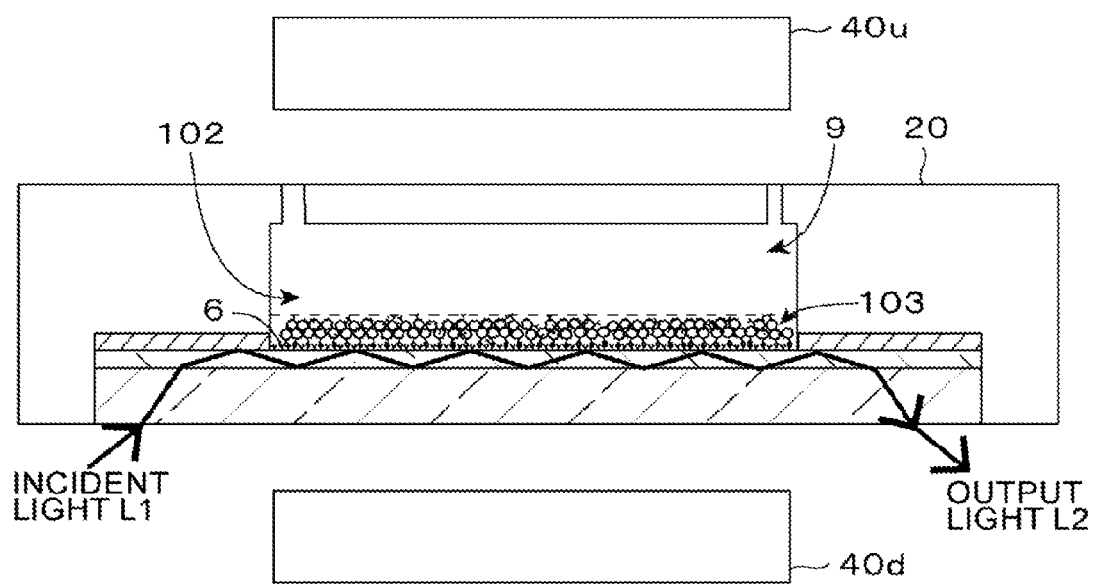
FIG. 6C is a view of the reaction space at a predetermined time.

Next, with reference to FIGS. 6A to 6C, a description is given of the action of the solid dispersion elements 9 in the spontaneous precipitation step $T_0$. FIG. 6A is a cross-sectional view illustrating the state in the reaction space 102 at the time $t=t_3$. FIG. 6B is a cross-sectional view illustrating the state in the reaction space 102 at the time $t=\tau_3$ ($t_3<\tau_3<t_4$). FIG. 6C is a cross-sectional view illustrating the state in the reaction space 102 at the time $t=\tau_4$ ($t_4 \leq T_4 < t_5$).

In the spontaneous precipitation step $T_0$, the value of the intensity ratio A converges to a second predetermined value after the decrease phase and the convergence phase. In this step, gravity as well as the lower magnetic field is applied to the solid dispersion elements 9. In the spontaneous precipitation step $T_0$, the solid dispersion elements 9 bind to the sensing surface 101 by the antibody-antigen reaction. In the phases illustrated in FIGS. 6A to 6C, at least part of the antigen 14 sequentially binds to the second antibodies 13.

At the time $t=t_2$, when the application of the lower magnetic fields is stopped, the solid dispersion elements 9 start spontaneously precipitating as being free from the restraining influence of the lower magnetic field. As illustrated in FIG. 6A, the state in the reaction space 102 immediately after the stop of the application of the lower magnetic fields is almost the same as the state illustrated in FIG. 5C.

In the section C2 to C3 of the curve 301 corresponding to a period $t_2$ to $t_3$, overshoot 310 occurs. The overshoot 310 is presumably caused by noise current generated when the operation of the lower magnetic field applicator 40d is terminated. The noise current may be, for example, stray current, inrush current, or the like. Due to the noise current, a reverse magnetic field is instantaneously generated, and thereby the solid dispersion elements 9 are lifted upward. With this, part of the solid dispersion elements 9 is instantaneously separated from the sensing area 103. Thus, the curve 301 represents the overshoot 310. At the time $t_3$, the noise caused by the overshoot 310 settles down. The time taken for the noise to settle down is known, and is stored in the memory circuit 90 in advance. The time may be experimentally obtained beforehand.

As illustrated in FIG. 6B, as being free from the restraining influence of the lower magnetic field, arrays of the solid dispersion elements 9 collapse, and randomly precipitate toward the sensing surface 101. In a period $t_3$ to $t_4$ illustrated in FIG. 6B, the solid dispersion elements 9 sequentially enter the sensing area 103, and accordingly, the curve 301 represents the decrease phase in which the intensity ratio A decreases at the initial stage. When the entry reaches saturation, the curve 301 represents the convergence phase. Specifically, the intensity ratio A decreases at high rate from the time $t=t_3$. The decrease rate is maintained for a predetermined period of time and gradually lowers. At the time $t=t_4$, the decrease rate of the intensity ratio A is almost zero. At the time $t=t_4$, the intensity ratio A converges to $A_2$ (the intensity ratio $A=A_2$) as the second predetermined value.

As illustrated in FIG. 6C, after the intensity ratio A becomes the second predetermined value, the solid dispersion elements 9 in the reaction space 102 are almost accumulated on the sensing surface 101. At this time, at least part of the solid dispersion elements 9 in contact with the sensing surface 101 specifically binds to the sensing surface 101 via the antigen 14. The solid dispersion elements 9 are accumulated in arrays on the sensing surface 101. The solid dispersion elements 9 are further accumulated on the arrays of the solid dispersion elements 9 accumulated. With this, the sensing area 103 is occupied by the solid dispersion elements 9 with almost no space. At the time $t=t_4$, the intensity ratio A converges to the second predetermined value. This value is substantially unchanged until the time $t=t_5$. This indicates that in a period $t_4$ to $t_5$, the solid dispersion elements 9 that newly enter the sensing area 103 substantially do not exist. In other words, at the time $t=t_4$, the precipitation to the sensing area 103 is substantially completed. In the sensing area 103, at least part of the solid dispersion elements 9, which are yet to be bound to the sensing surface 101 at the time $t=t_4$, binds to the sensing surface 101 in a period $t_4$ to $t_5$.

(Upper Magnetic Field Application Step, Measurement Step)

Figure 7:
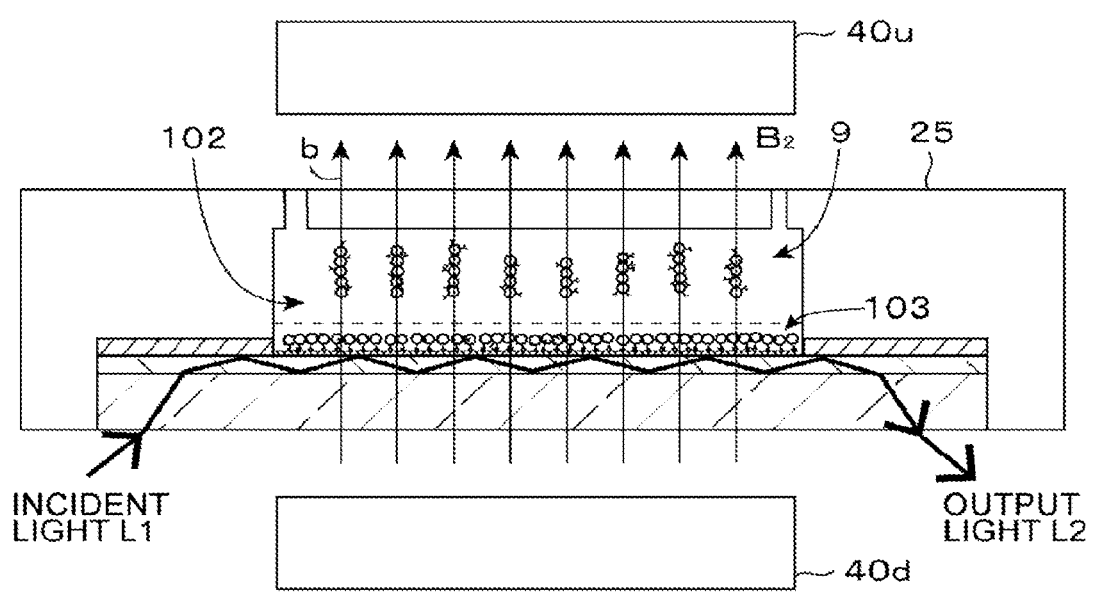
FIG. 7 is a view of the reaction space at a predetermined time.

With reference to FIG. 7, a description is given of the action of the solid dispersion elements 9 in the upper magnetic field application step $U_0$. FIG. 7 is a cross-sectional view illustrating the state in the reaction space 102 at the time $t=\tau_5$ ($t_6 \leq \tau_5 \leq t_7$). At the time $t=t_7$, the measurement step $V_0$ is performed.

In the upper magnetic field application step $U_0$, the value of the intensity ratio A converges to a third predetermined value after the increase phase and the convergence phase. In this step, gravity and the upper magnetic field are applied to the solid dispersion elements 9. Accordingly, the solid dispersion elements 9 not binding to the sensing surface 101 by the antibody-antigen reaction separate from the sensing area 103.

After the spontaneous precipitation, the application of the upper magnetic fields is started. In FIG. 7, upward arrows indicate the direction of a magnetic flux $B_2$ generated due to the application of the upper magnetic field. The magnetic flux $B_2$ is formed of a plurality of magnetic lines b, and penetrates upward through the reaction space 102.

The state in the reaction space 102 immediately after the stop of the spontaneous precipitation is almost the same as the state illustrated in FIG. 6C. That is, at the time immediately before time $t=t_5$, the solid dispersion elements 9 are accumulated in arrays on the sensing surface 101, and many of the solid dispersion elements 9 in contact with the sensing surface 101 specifically bind to the sensing surface 101.

When the upper magnetic field is applied to the reaction space 102, an upward magnetic force is applied to the solid dispersion elements 9. This magnetic force is larger than the gravity and smaller than the binding force by the antibody-antigen reaction in the sensing area 103. Accordingly, by the application of the upward magnetic force, the solid dispersion elements 9 not specifically binding to the sensing surface 101 separate from the sensing area 103. Thus, the value of the intensity ratio A sharply increases upon arrival of the time $t=t_5$.

In a period $t_5$ to $t_6$, the curve 301 represents overshoot 311. After the overshoot 311, the curve 301 represents convergence to the third predetermined value after the decrease phase and the convergence phase. The overshoot 311 is presumably caused by the same factors as described above for the overshoot 310. That is, due to an inrush current or the like, an upward magnetic force larger than the binding force by the antibody-antigen reaction is applied to the solid dispersion elements 9 in the sensing area 103. With this, the bond by the antibody-antigen reaction is instantly broken, and the solid dispersion elements 9 bound to the sensing surface 101 separate from the sensing area 103. When the electric current is stabilized, the magnetic force becomes smaller than the binding force by the antibody-antigen reaction. The solid dispersion elements 9 separated are bound again to the sensing surface 101. Due to this rebinding, after the time $t=t_5$, the intensity ratio A starts decreasing at high rate. The decrease rate is maintained for a predetermined period of time and gradually lowers. At the time $t=t_6$, the decrease rate of the intensity ratio A is almost zero. At the time $t=t_6$, the intensity ratio A converges to $A_3$ (the intensity ratio $A=A_3$) as the third predetermined value.

After the intensity ratio A converges to $A_3$, there are only the solid dispersion elements 9 that specifically bind to the sensing surface 101 via the antigen 14 in the sensing area 103 (see FIG. 7). In other words, the other solid dispersion elements 9 are located out of the sensing area 103 due to the upper magnetic field.

At the time $t=t_7$ after the lapse of a predetermined time from the convergence of the intensity ratio A to $A_3$ as the third predetermined value, the measurement step $V_0$ is performed. A period $t_5$ to $t_7$ is the time required to be ready for measurement. The time required to be ready for measurement is known. This time is stored in the memory circuit 90 as the setting information. Specifically, the system control circuit 70 extracts the intensity ratio $A_3$ corresponding to the time $t=t_7$, and sends it to the information generating circuit 65. The information generating circuit 65 obtains the amount of the antigen 14 corresponding to the intensity ratio $A_3$ extracted based on correspondence information between the intensity ratio A and the amount of the antigen 14. The information generating circuit 65 then generates information indicating measurement results based on the amount of the antigen 14.

<Memory Circuit>

The memory circuit 90 stores information received from the detector 50 or the operation circuit (not illustrated). In addition, the memory circuit 90 stores the setting information in advance. The setting information includes information indicating types of a plurality of steps performed to measure the amount of the antigen 14 present in the reaction space 102, information indicating the order of the transition of the steps, and information indicating the timing of the transition between the steps. Note that the setting information may include a plurality of sets of these pieces of information associated with one another. In this case, an arbitrary set of information is selected manually or automatically for use in a test.

Further, the memory circuit 90 stores reference information used in determining the step transition timing. The reference information is used by the transition timing specifying circuit 80. The information is stored in/retrieved from the memory circuit 90 by the system control circuit 70.

<Output Unit>

The output unit 60 outputs information received from the detector 50 or the operation circuit (not illustrated) under the control of the system control circuit 70. The output unit 60 includes the display 61 and a notification unit 62. The display 61 displays information under the control of the system control circuit 70. For example, the display 61 displays a graph indicating a time-series variation in the intensity ratio as illustrated in FIG. 4, information related to a specimen, and the like. The notification unit 62 outputs a predetermined operation sound or a warning sound under the control of the system control circuit 70. Incidentally, the display 61 may have the notification function. The output unit 60 need not necessarily output the information in this manner, but may have functions for transmitting the information to the outside via a network or the like, writing the information to a recording medium, and the like.

<Transition Timing Specifying Circuit>

The transition timing specifying circuit 80 has the function of specifying step transition timing based on information of the output light L2. As an example, the transition timing specifying circuit 80 has the function of specifying transition timing based on a time-series variation in the light intensity. The transition timing specified is not limited to the timing of transition from one step to the next, but may include the timing of the start of any step performed after the step. To specify the transition timing, for example, the transition timing specifying circuit 80 has the following functions. In the description of the functions, the above-mentioned intensity ratio is described as information indicating the intensity of the output light L2. However, the information is not limited thereto, and may be information related to the intensity of the output light L2 (i.e., any information obtained from the detection result of the intensity of the output light L2) such as the absolute intensity of the output light L2, the relative intensity between the incident light L1 and the output light L2.

(First Function)

The transition timing specifying circuit 80 sequentially receives information on the intensity ratio in real time from the processing circuit 53. The transition timing specifying circuit 80 has the function of monitoring the time-series variation in the light intensity ratio based on the information to thereby specify the step transition timing (herein sometimes referred to as "first function").

Described below is an example of the process of monitoring the time-series variation in the light intensity ratio. Each time receiving the value of the intensity ratio, the transition timing specifying circuit 80 calculates the change rate of the intensity ratio based on at least part of the history of values of the intensity ratio obtained up to this point, and compares the change rate to a default value. The transition timing specifying circuit 80 determines the transition timing based on the comparison result. The default value may be experimentally obtained, for example.

For example, in the example of FIG. 4, the change rate corresponds to the inclination of the curve 301 (always being a negative value or zero). Besides, the default value $\alpha$ is substantially zero. In this case, the transition timing specifying circuit 80 compares the value of inclination to the default value $\alpha$. When the former is above the latter, the transition timing specifying circuit 80 determines that it is time to transit to the next step.

For another example, the transition timing specifying circuit 80 may determine whether the value of inclination stays above the default value $\alpha$ for a predetermined period of time to determine the arrival of the transition timing to the next step. In this example, the stabilization of the value of inclination (i.e., the stabilization of the intensity ratio, or the stabilization of the movement of the solid dispersion elements 9 in the sensing area 103) may be used as a trigger for transition between steps.

For still another example, the transition timing specifying circuit 80 may determine, as the transition timing, the time point at which the sum of periods (accumulated time) for which the intensity ratio and the default value are in predetermined relationship or the number of times (accumulated number of times) they are determined to be in the relationship exceeds a predetermined threshold.

The transition timing specifying circuit 80 may specify or estimate transition timing to a still later step (second transition timing) based on the transition timing (first transition timing) specified as above. This is because it is possible to estimate the degree of the progress of the antibody-antigen reaction in the reaction space 102 based on the first transition timing. For example, a measurement flow including the first, second, and third state change steps is to be considered below. The transition timing specifying circuit 80 specifies the first transition timing from the first state change step to the second state change step using the first function. The transition timing specifying circuit 80 further specifies the second transition timing from the second state change step to the third state change step based on the first transition timing. This specifying process is performed, for example, based on the time required for the first state change step. That is, if the first state change step has required a short time, it can be assumed that the antibody-antigen reaction progresses quickly in the reaction space 102. Therefore, based on this determination result, the time required for the second state change step is estimated. This process may be performed, for example, with reference to correspondence information in which the time taken for the second state change step is associated with the time taken for the first state change step. For example, the correspondence information is stored in the memory circuit 90 in advance. Besides, the correspondence information can be empirically and experimentally obtained. Note that the first transition timing is not necessarily the earliest transition timing specified by the transition timing specifying circuit 80. In addition, the transition timing estimated as above may be changed or adjusted depending on the state after the transition timing estimated or user's determination.

(Operation of the Specimen Measurement Apparatus)

Described below is an example of the measurement flow performed by the specimen measurement apparatus 10 of the embodiment. The specimen measurement apparatus 10 operates as follows, for example, so that the step transition timing of the measurement flow can be variable.

(Change Step Transition Timing)

Figure 8:
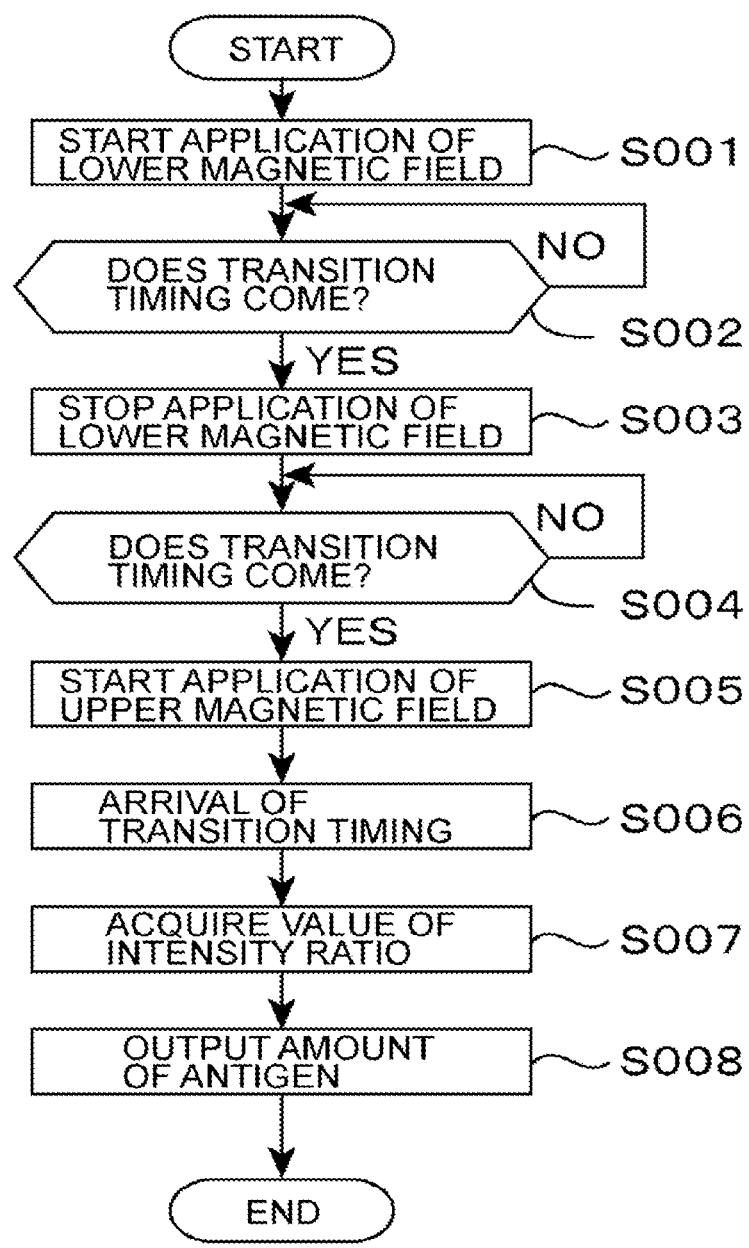
FIG. 8 is a flowchart of an example of the operation of the specimen measurement apparatus in the first embodiment.

FIG. 8 is a flowchart of an example of the operation of the specimen measurement apparatus 10 to measure the amount of the antigen 14 contained in a sample liquid. The following description is made with reference to FIGS. 4 to 7 as appropriate. The system control circuit 70 controls the specimen measurement apparatus 10 according to the measurement flow based on the setting information stored in the memory circuit 90 in advance to obtain the amount of the antigen 14 contained in a sample liquid.

Figure 9:
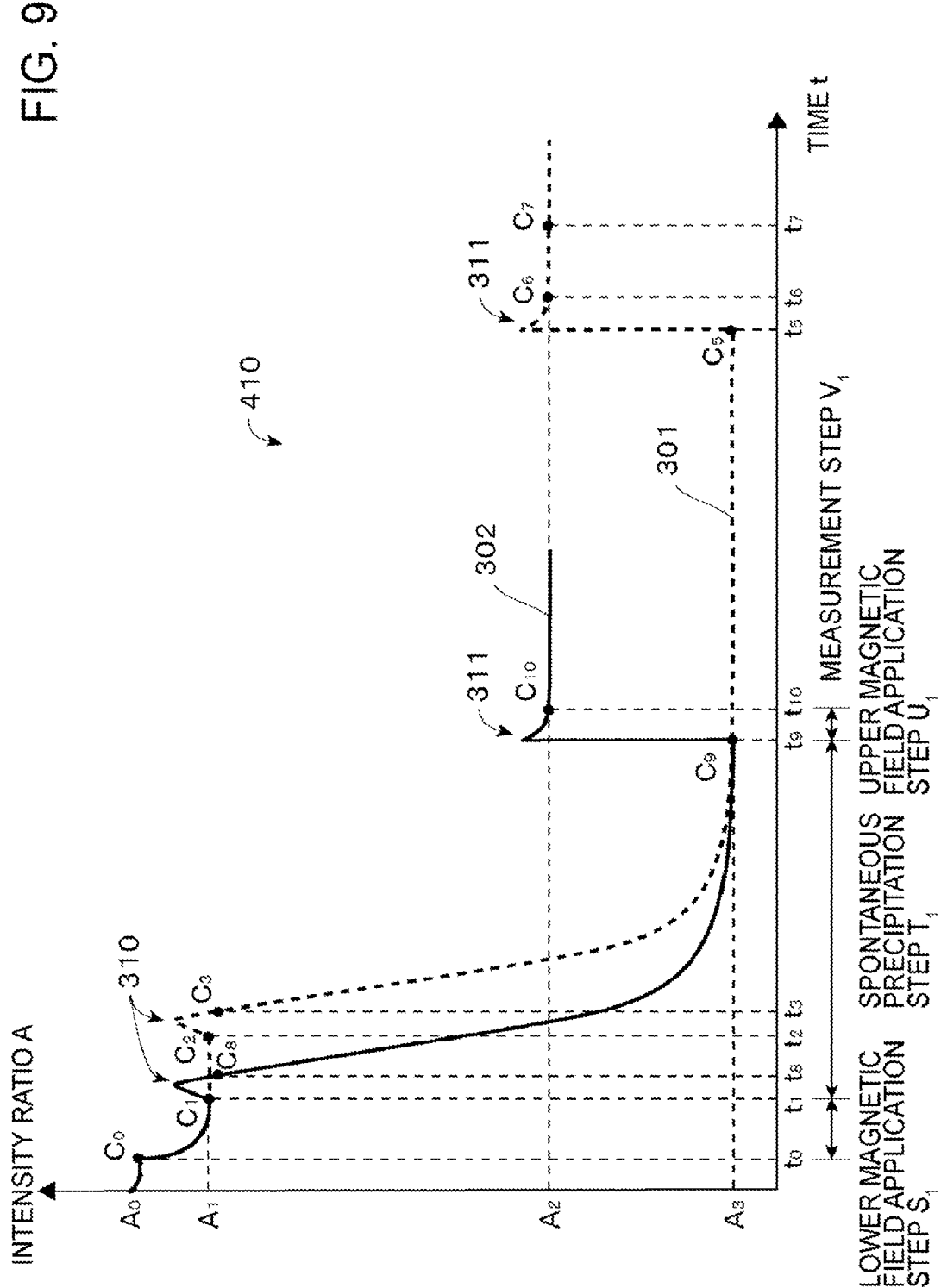
FIG. 9 is a graph illustrating a time-series variation in the intensity ratio of output light.

FIG. 9 is a graph 410 illustrating a time-series variation in the intensity of the output light L2 detected in the measurement. In FIG. 9, a solid curve 302 indicates a time-series variation in the intensity of the output light L2 detected in the measurement in which the transition timing is changed. The dashed curve 301 indicates a time-series variation in the intensity of the output light L2 detected in the ordinary measurement. In the graph 410, the curve 301 corresponding to the ordinary measurement is represented by a dashed line, while the curve 302 corresponding to the measurement in which the transition timing is changed is represented by a solid line. In the following, FIG. 9 is used as appropriate.

Triggered by the fact that the reaction case 20 is mounted on the specimen measurement apparatus 10 and the introduction of a test liquid into the reaction space 102 is completed, the system control circuit 70 starts the measurement flow. For example, the system control circuit 70 starts controlling the lower magnetic field applicator 40d based on the setting information. With this, the lower magnetic field applicator 40d applies a lower magnetic field to the reaction space 102 (step S001). As illustrated in FIG. 9, the application of the lower magnetic field is started at the time $t=t_0$ as in an ordinary manner. Thus, the lower magnetic field application step $S_1$ is started.

Then, the transition timing specifying circuit 80 obtains transition timing based on the degree of precipitation of the solid dispersion elements 9 using the first function. For example, each time receiving the value of the intensity ratio, the transition timing specifying circuit 80 calculates the change rate of the intensity ratio based on at least part of the history of values of the intensity ratio obtained up to this point, and compares the change rate (a negative value or zero) to the default value α (substantially zero). The transition timing specifying circuit 80 determines the transition timing based on the comparison result (step S002). Incidentally, the change rate is a decrease rate indicated by the curve 302 in the decrease phase from the time $t_0$ in FIG. 9. A state where the change rate is equal to or above the default value α corresponds to a state where the decrease has converged in the decrease phase (convergence phase). This state of convergence is indicated at the time $t_1$ corresponding to the transition timing in FIG. 9. The lower magnetic field application step $S_1$ is performed in a period $t_0$ to $t_1$ in the curve 302.

The application of the lower magnetic field is continued until the change rate obtained by the transition timing specifying circuit 80 becomes equal to or above the default value α (NO in step S002). When the change rate becomes equal to or above the default value α (YES in step S002), the transition timing specifying circuit 80 outputs the result to the system control circuit 70. This state indicates that the solid dispersion elements 9 have sufficiently moved due to the lower magnetic field, and the movement of them almost stops in the sensing area 103.

Having received the result, the system control circuit 70 stops the application of the lower magnetic field, and thus the application ends (step S003). That is, a transition occurs from the lower magnetic field application step $S_1$ to the spontaneous precipitation step $T_1$ (FIG. 9).

Also in the spontaneous precipitation step $T_1$, the transition timing specifying circuit 80 obtains transition timing based on the degree of precipitation of the solid dispersion elements 9 using the first function. In other words, the transition timing specifying circuit 80 obtains the transition timing to the next step (e.g., the upper magnetic field application step $U_1$) based on the result of the comparison between the change rate and the default value α (step S004). Incidentally, the change rate is a decrease rate indicated by the curve 302 in the decrease phase from the time $t_8$ in FIG. 9. In a period $t_1$ to $t_8$, the overshoot 310 occurs. The time $t_8$ may be set as with the time $t_3$ in FIG. 4. A state where the change rate is equal to or above the default value α corresponds to a state where the decrease has converged in the decrease phase (convergence phase). This state of convergence is indicated at the time $t_9$ corresponding to the transition timing in FIG. 9. The spontaneous precipitation step $T_1$ is performed in a period $t_1$ to $t_9$ in the curve 302.

The monitoring based on the first function may be continued from step S002 through S004, or it may be once stopped by the transition to step S003 and resumed in step S004.

The transition timing specifying circuit 80 continues to monitor the degree of precipitation of the solid dispersion elements 9 in the spontaneous precipitation step $T_1$ without transition to the next step until the change rate becomes equal to or above the default value α (NO in step S004). When the change rate becomes equal to or above the default value α (YES in step S004), the transition timing specifying circuit 80 outputs the result to the system control circuit 70. Having received the result, the system control circuit 70 starts the application of the upper magnetic field (step S005). That is, a transition occurs from the spontaneous precipitation step $T_1$ to the upper magnetic field application step $U_1$ (FIG. 9). The transition timing is the time $t_9$ at which the decrease is determined to have converged in the decrease phase (convergence phase) of the spontaneous precipitation step $T_1$ as well. In FIG. 9, the spontaneous precipitation step $T_1$ corresponds to a period $t_1$ to $t_9$ indicated by the curve 302. That is, this state indicates that the movement of the solid dispersion elements 9 almost stops in the sensing area 103, and also that the solid dispersion elements 9 have sufficiently moved by spontaneous precipitation or diffusion due to gravity in this step.

The monitoring based on the first function may be continued from step S002 through S004, or it may be once stopped by the transition to step S003 and resumed in step S004.

The transition timing specifying circuit 80 acquires the time required to be ready for the measurement from the setting information, and specifies the transition timing from the upper magnetic field application step $U_1$ to the measurement step $V_1$ based on the time. Upon arrival of the transition timing (step S006), the information generating circuit 65 acquires the value of the intensity ratio A (step S007), and generates information indicating the amount of the antigen 14 in the reaction space 102 based on the intensity ratio A. This information is output through the output unit 60 to the outside (step S008). With this, the process ends.

In this flowchart, the process is performed such that, if the antibody-antigen reaction progresses faster than usual in the sensing surface 101, the measurement is accelerated as compared to the ordinary measurement. However, this is not so limited, and may be applicable to the case where the antibody-antigen reaction progresses slowly in the sensing surface 101. In this case, the period $t_0$ to $t_1$ (lower magnetic field application step $S_1$) and the period $t_1$ to $t_9$ (spontaneous precipitation step $T_1$) in FIG. 9 are set longer than usual. Besides, the transition timing from the upper magnetic field application step $U_1$ to the measurement step $V_1$ may be set at the point when the change rate of the intensity ratio A becomes equal to or above the default value α. For example, this point may be at the time $t=t_{10}$.

According to this embodiment, the specimen measurement apparatus 10 can reduce the time required to measure the amount of the antigen 14 depending on the situation. The measurement flow represented by the curve 301 is compared below to that represented by the curve 302. The lower magnetic field application step $S_1$ is performed in a period $t_0$ to $t_1$. This means that the time taken for the lower magnetic field application step $S_1$ can be reduced by a period $t_2-t_1$. Besides, the spontaneous precipitation step $T_1$ is performed in a period $t_1$ to $t_9$. This means that the time taken for the spontaneous precipitation step $T_1$ can be reduced by a period $t_5-t_4$. The upper magnetic field application step $U_1$ is performed in a period $t_9$ to $t_{10}$. This means that the time taken for the upper magnetic field application step $U_1$ can be reduced by a period $t_7-t_6$. Through the reduction of time, the entire measurement can be shortened by, for example, 5 minutes.

In the measurement by the specimen measurement apparatus 10 of this embodiment, the antibody-antigen reaction needs to have progressed to a level that guarantees the measurement accuracy at the point of transition to the upper magnetic field application step $U_1$. For example, the antibody-antigen reaction needs to be steady. However, this is not so limited, and the antibody-antigen reaction may only be required to have progressed to a level where a qualitative determination can be made.

In the following, first time and second time are discussed. The first time is the time (precipitation time) taken for the solid dispersion elements 9 to move to the sensing area 103 due to a magnetic force and gravity. The second time is the time (measurement available time) spent until the antibody-antigen reaction has progressed to a level that guarantees the measurement accuracy. In this case, the antibody-antigen reaction indicates that the solid dispersion elements 9 move to the sensing area 103 and also bind to the sensing surface 101 via the antigen 14.

According to the embodiment, the specimen measurement apparatus 10 is capable of constructing the measurement flow taking into account the first time and the second time. As described above, the first time can be acquired from a time-series variation in the intensity ratio A. The specimen measurement apparatus 10 can specify the second time based on, for example, concentration information (information serving as an index of the concentration) of the antigen 14 retained in the reaction space 102. The concentration information of the antigen 14 can be acquired from the time-series variation in the intensity ratio A. The acquisition of the concentration information is described later.

According to the embodiment, the specimen measurement apparatus 10 may be configured to prompt the operator to select whether to use the first function of the transition timing specifying circuit 80 in consideration of the type of a test item to be measured and the like. For example, if a test item to be measured is a specific test item, the operator selects to use the first function. For example, the specific test item is the one that allows the test result to be fixed by qualitative determination. The test item that allows the test result to be fixed by qualitative determination is, for example, a test item for which a positive result can be achieved by detecting a predetermined amount of the antigen 14. Examples of the specific test item include a test item for determining infection by a virus or the like. With this test item, when the amount of the antigen 14 exceeds a threshold, a positive result can be obtained. Among test items that allow the test result to be fixed by qualitative determination, for example, the specific test item is preferably the one with the threshold of a very small value.

Further, according to the embodiment, the specimen measurement apparatus 10 can estimate step transition timing from a decrease period in which the intensity ratio A decreases in time-series variation. The decrease period is, for example, a period $t_3$ to $t_4$ in FIG. 4. That is, based on a period from the start of a step to the transition timing estimated by the first function, transition timing to the following steps can be estimated. The period is related to the degree of the progress of the antibody-antigen reaction (hereinafter sometimes referred to as "reaction progress degree") as well as the movement of the solid dispersion elements 9. That is, if the period is short, it indicates that the antibody-antigen reaction progresses quickly. The reaction in the "reaction progress degree" refers to a reaction in which the solid dispersion elements 9 bind to the sensing surface 101 via the antigen 14 or a reaction in which the solid dispersion elements 9 bind together via the antigen 14. The "reaction progress degree" may be determined by, for example, a plurality of parameters related to the reaction progress degree. The parameters include, for example, the concentration of the antigen 14, the concentration of the first antibodies 6, and the concentration of the second antibodies 13. For example, the concentration of the antigen 14 can be derived from the "reaction progress degree" by fixing the densities of the first antibodies 6 and the second antibodies 13.

[Modification]

As described above, in one example, the specimen measurement apparatus 10 is configured to prompt the operator to select whether to perform the first function of the transition timing specifying circuit 80 in consideration of the type of a test item to be measured by the operator. However, the specimen measurement apparatus 10 of the first embodiment is not so limited. For example, the specimen measurement apparatus 10 of this embodiment may include a determination circuit to automatically make the selection.

Figure 10:
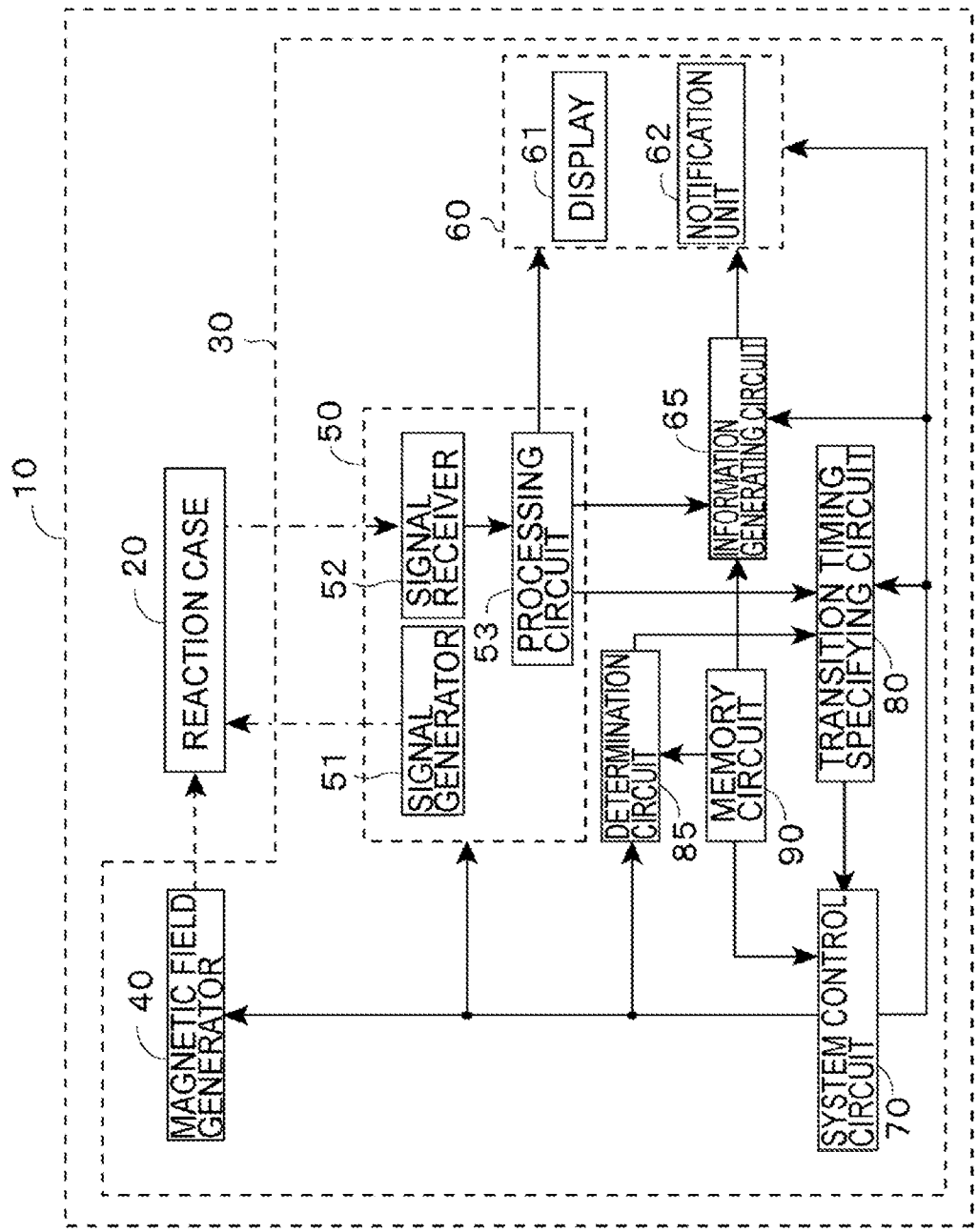
FIG. 10 is a block diagram of an example of the entire configuration of a specimen measurement apparatus according to a modification.

FIG. 10 is a block diagram of an example of the entire configuration of the specimen measurement apparatus 10 according to a modification of the embodiment. As illustrated in FIG. 10, the specimen measurement apparatus 10 of this modification further includes a determination circuit 85.

<Determination Circuit>

The determination circuit 85 determines whether a measurement to be performed is of a specific test item. Test information for setting test item includes identification information. The identification information indicates, for example, types of test items. In this modification, instead of the operator, the determination circuit 85 determines whether to perform the first function of the transition timing specifying circuit 80 in consideration of the type of the test item or the like.

Described below is an example of the determination process performed by the determination circuit 85.

First, the determination circuit 85 acquires information on a test item to be measured from the test information. The determination circuit 85 determines whether the test item is the specific test item. Having determined that the test item is the specific test item, the determination circuit 85 outputs the determination result to the transition timing specifying circuit 80. Upon receipt of the determination result, the transition timing specifying circuit 80 starts the process of specifying step transition timing.

That is, when the determination circuit 85 determines that a test item to be measured is the specific test item, "specific measurement" is performed in which the above control is performed to allow the step transition timing to be variable in the measurement flow. On the other hand, when the determination circuit 85 determines that a test item to be measured is not the specific test item, upon receipt of the determination result, the system control circuit 70 performs control based on the setting information for "ordinary measurement".

When conducting an "ordinary measurement", the system control circuit 70 controls each unit of the specimen measurement apparatus 10 to perform a plurality of steps in order. Thus, the amount of a test substance in the reaction case 20 can be measured. On the other hand, when performing a "specific measurement" that satisfies specific conditions, the specimen measurement apparatus 10 specifies the step transition timing based on a detection signal.

(Operation of the Specimen Measurement Apparatus)

In the following, an example of the measurement flow performed by the specimen measurement apparatus 10 of this modification. The specimen measurement apparatus 10 operates as follows, for example, to allow the step transition timing in the measurement flow to be variable when a specific measurement is to be performed.

Figure 11:
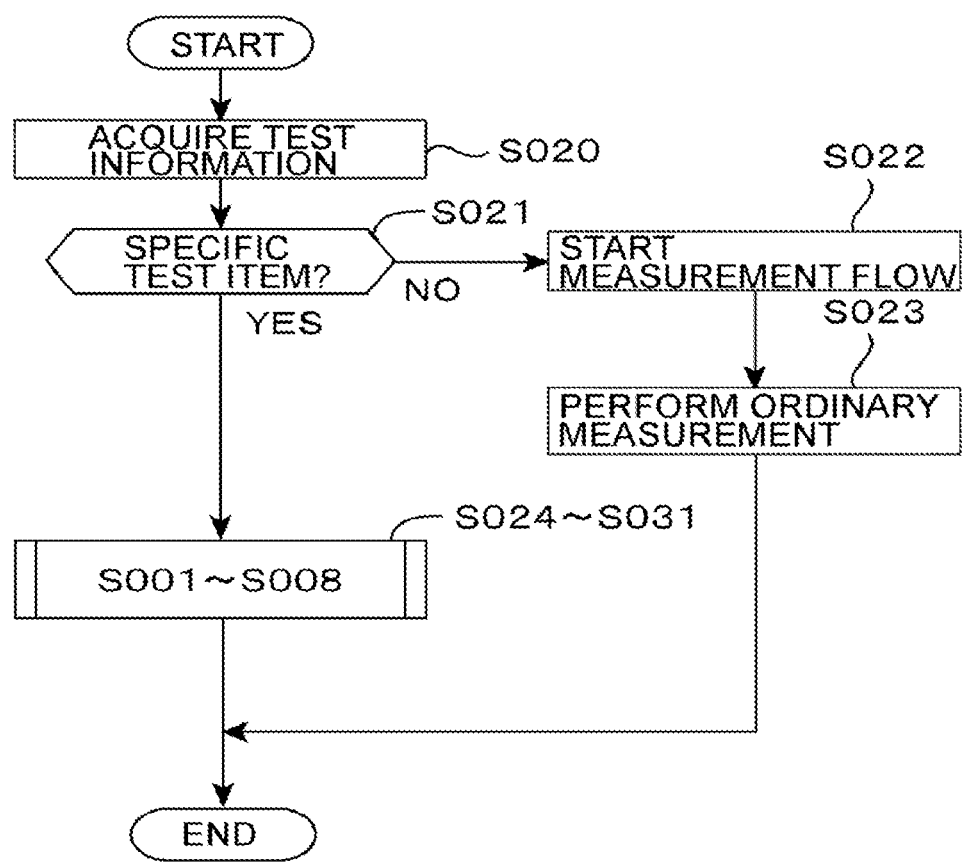
FIG. 11 is a flowchart of an example of the operation of a specimen measurement apparatus in the modification.

FIG. 11 is a flowchart of an example of the operation of the specimen measurement apparatus 10 to measure the amount of the antigen 14 contained in a sample liquid. In the flowchart, first, it is determined whether an object to be measured is a specific test substance before the start of measurement. When the measurement object is a specific test substance, the specimen measurement apparatus changes the step transition timing from ordinary timing. The following description is made with reference to FIGS. 4 to 7 as appropriate.

Before the start of measurement, the determination circuit 85 acquires the test information for a measurement to be performed (step S020). Then, the determination circuit 85 determines whether a test item to be measured is the specific test item (step S021). In addition, the determination circuit 85 determines whether the test item to be measured is of a type that allows the test result to be fixed by qualitative determination. If not, the determination circuit 85 determines that the test item is not the specific test item (NO in step S021). The determination circuit 85 outputs the determination result to the system control circuit 70. Upon receipt of the determination result, the system control circuit 70 starts the measurement flow (step S022). In this case, an ordinary measurement set in advance is performed (step S023). In the ordinary measurement, for example, steps transition from one to another at timing determined in advance as illustrated in FIG. 4. The setting information for the ordinary measurement is stored in the memory circuit 90 in advance. The system control circuit 70 controls the specimen measurement apparatus 10 based on the setting information, and obtains the amount of the antigen 14.

Having determined that the test item is of a type that allows the test result to be fixed by qualitative determination, the determination circuit 85 determines that the test item is the specific test item (Yes in step S021). The determination circuit 85 outputs the determination result to the system control circuit 70. Thereafter, a process is started to make the step transition timing of the measurement flow variable. The process can be performed in the same manner as steps S001 to S008 in FIG. 8 (steps S024 to S031).

According to this embodiment, transition timing between at least part of steps in a measurement flow can be variable based on information indicating a time-series variation in the intensity of light output from the reaction case 20. Specifically, when a test item to be measured is a specific test item, the specimen measurement apparatus 10 sets the time at which precipitation of the solid dispersion elements 9 is completed as transition timing. Besides, the specimen measurement apparatus 10 of this embodiment can estimate the step transition timing based on a decrease period in which the intensity ratio of output light decreases. For example, if the decrease period is short, it indicates that the antibody-antigen reaction progresses quickly. Therefore, the step transition timing can be put forward as compared to the ordinary measurement.

Second Embodiment

The specimen measurement apparatus 10 of a second embodiment is of basically the same configuration as that of the first embodiment. Therefore, the specimen measurement apparatus 10 of this embodiment is described with reference to FIG. 1 as appropriate. The specimen measurement apparatus 10 of this embodiment is different from that of the first embodiment in that the reaction progress degree between a test substance and a reagent is determined from a time-series variation in the intensity of the output light L2, and the step transition timing is specified based on the determination result.

<Transition Timing Specifying Circuit>

The transition timing specifying circuit 80 specifies the reaction progress degree between a test substance and a reagent from a time-series variation in the intensity of the output light L2, and specifies the step transition timing based on the specified result. The transition timing specifying circuit 80 can specify the reaction progress degree between a test substance and a reagent from information on the light intensity. For example, assuming that the test substance is the antigen 14 and the reagent is an antibody, the transition timing specifying circuit 80 can specify the degree of the progress of the antibody-antigen reaction between them. The transition timing specifying circuit 80 has second and third functions for this specifying process.

The first function described above is capable of specifying the timing at which the movement of the solid dispersion elements 9 becomes steady in the sensing area 103 based on a time-series variation in the light intensity ratio. On the other hand, the second and third functions are capable of specifying the degree of the progress of the antibody-antigen reaction based on a time-series variation in the light intensity ratio, and specifying the timing at which the antibody-antigen reaction has progressed to a level that guarantees the measurement accuracy based on the degree of the progress. Further, based on the degree of the progress or the state of the movement of the solid dispersion elements 9, the transition timing can be put forward as compared to the ordinary measurement. In the specimen measurement apparatus 10 of this embodiment, for example, the first function can be combined with the second or third function. By the combination of the functions, the transition timing specifying circuit 80 can specify the timing at which the movement of the solid dispersion elements 9 becomes steady in the sensing area 103 as well as the timing at which the antibody-antigen reaction has progressed to a level that guarantees the measurement accuracy. For example, by setting later one of the timings as the step transition timing, a measurement can be performed at a timing at which the movement of the solid dispersion elements 9 becomes steady and the antibody-antigen reaction has progressed to a level that guarantees the measurement accuracy.

(Second Function)

The second function specifies the degree of the progress of the antibody-antigen reaction in the reaction space 102 based on the degree of the variation of the intensity of the output light L2 obtained in the early time of the steps. One example is described with reference to FIG. 4. As described above, a time-series variation in the intensity ratio A represented by the curve 301 represents the decrease phase in the early time of each step. The decrease phase corresponds to, for example, a period $t_0$ to $t_1$ in the lower magnetic field application step $S_0$. The decrease phase may be set in a period $t_0$ to $t_1$. This period is, for example, $t_0$ to $t_P$. The time $t_P$ is set by the expression, $t_P = t_0 + ((t_1 - t_0)/P)$. The constant P may be set in the range of 3 to 10. The decrease phase (early time) corresponds to, for example, a period $t_3$ to $t_Q$ in the lower magnetic field application step $S_0$. The decrease phase may be set in a period $t_3$ to $t_4$. This period is, for example, $t_3$ to $t_R$. The time $t_Q$ is set by the expression, $t_Q = t_3 + ((t_4 - t_3)/P)$. The constant Q may be set in the range of 3 to 10. The transition timing specifying circuit 80 obtains the degree of the decrease of the intensity ratio A in the decrease phase, and specifies the degree of the progress of the antibody-antigen reaction based on the degree of the decrease.

Described below is how to specify the degree of the progress of the antibody-antigen reaction based on the decrease of the intensity ratio A. The degree of the decrease of the intensity ratio A in the decrease phase indicates the state of the movement of the solid dispersion elements 9. Specifically, the degree of the decrease indicates the degree of the increase of the solid dispersion elements 9 in the sensing area 103. The solid dispersion elements 9 precipitate in the reaction space 102 by, at least, gravity.

In the reaction space 102, as the concentration of the antigen 14 increases, the antigen 14 reacts with the antibody with a higher probability. Accordingly, the antibody-antigen reaction presumably progresses faster in the measurement. Meanwhile, when the solid dispersion elements 9 precipitate in the reaction space 102, the solid dispersion elements 9 may be aggregated via the antigen 14 and form an aggregate. For example, the high concentration of the antigen 14 causes an increase in the amount of the aggregate, resulting in an increase in the amount of the solid dispersion elements 9 aggregated in the aggregate. Therefore, when the solid dispersion elements 9 precipitate in the reaction space 102, more amount of the solid dispersion elements 9 enter the sensing area 103. The increase of the amount raises the degree of the decrease of the intensity ratio A in the decrease phase. Thus, the reaction progress degree can be specified in the step based on the degree of the decrease of the intensity ratio A in the decrease phase.

As the degree of the decrease of the intensity ratio A, for example, the decrease rate of the intensity ratio A above mentioned or a difference in the intensity ratio A in a specific period is obtained. Examples of the value of the decrease rate of the intensity ratio A include the value of the decrease rate at a specific time and the value of the average decrease rate in a specific period. While any one of them may be selected appropriately as the degree of the decrease of the intensity ratio A, for example, the average decrease rate in a specific period is employed. With the use of the average decrease rate, the influence of unintended noise can be reduced. In the following, an example is described in which the average decrease rate of the intensity ratio A in a specific period is used as the degree of the decrease of the intensity ratio A.

As the reaction progress degree, for example, a reaction rate may be obtained. That is, the transition timing specifying circuit 80 can obtain an antibody-antigen reaction rate from the average decrease rate in a specific period. When the antibody-antigen reaction progresses at a constant rate, the transition timing specifying circuit 80 can specify progression time $t_G$ sufficient for transition from one step to another based on the antibody-antigen reaction rate. The step from which the transition is made is either or both of a current step and a step subsequent thereto. When the antibody-antigen reaction does not progress at a constant rate, for example, the transition timing specifying circuit 80 can specify the progression time based on correspondence information. The correspondence information is empirically and experimentally obtained, and stored in the memory circuit 90 or the like in advance.

In the correspondence information, for example, the average decrease rate of the intensity ratio A is associated with the time required for reaction. The correspondence information is obtained by, for example, measuring a plurality of sample liquids in which the concentration of the antigen 14 is known and deriving the correspondence relationship from the measurement results. Examples of the correspondence relationship obtained include a correspondence table between the average decrease rate of the intensity ratio A and the time required for reaction, and a calibration curve with the horizontal axis indicating the average decrease rate of the intensity ratio A and the vertical axis indicating the time required for reaction. The transition timing specifying circuit 80 can estimate and obtain the concentration of the antigen 14 based on the correspondence information. The correspondence information may indicate correspondence between the change rate (decrease rate) of the intensity of the output light L2 and the concentration of the antigen 14.

The transition timing specifying circuit 80 may specify the time at which the reaction has progressed to a level that guarantees the measurement accuracy based on the time required for the reaction, for example, and thereby specify step transition timing. The correspondence information may be prepared for each step. Besides, when a different value is used as the degree of the decrease of the intensity ratio A, the correspondence information is determined according to the value. Examples of the different value include the decrease rate of the intensity ratio A at a predetermined time and a difference in the intensity ratio A in a specific period. The transition timing specifying circuit 80 specifies transition timing based on progression time $t_G$ sufficient for transition from one step to another. For example, in the lower magnetic field application step, the time when the time $t_G$ has elapsed from the time to may be determined as the transition timing.

The second function is capable of specifying the transition timing from one step to another based on the decrease phase in the early time of the step. Thus, the step transition timing specified with respect to a specific test item can be put forward as compared to the transition timing specified by the first function. Examples of the specific test item include, in addition to a test item that allows the test result to be fixed by qualitative determination, the antigen 14 the antibody-antigen reaction of which is remarkably fast, a test item using an antibody, and a test item that satisfies the both. Examples of the test item that allows the test result to be fixed by qualitative determination include, for example, measurement to make a determination about infection. As described above, when the amount of the antigen 14 exceeds a predetermined threshold, a positive result can be obtained. If the threshold is a very small value, and the antibody-antigen reaction progresses quickly, transition can be made from a current step to the measurement step before the completion of the step. The completion of the step may correspond to, for example, the completion of the precipitation of the solid dispersion elements 9.

The degree of the decrease of the intensity ratio A need not necessarily be obtained at a time (in a period) set in advance. For example, the degree of the decrease of the intensity ratio A may be sequentially obtained by monitoring.

In this case, for example, the transition timing specifying circuit 80 obtains the decrease rate of the intensity ratio A each time the value of the light intensity is obtained in the same manner as described previously for the first function. The transition timing specifying circuit 80 detects whether the decrease rate thus obtained reaches a threshold. The threshold may be set to a predetermined range, or there may be a plurality of thresholds. When a plurality of thresholds are used, the transition timing specifying circuit 80 performs the detection using the thresholds in order from the smallest. Thus, the decrease rate of the intensity ratio A can be detected in stages.

The transition timing specifying circuit 80 ends the detection with the largest of the thresholds. The detection also ends when performed for a predetermined period of time. If the decrease rate of the intensity ratio A does not reach the smallest threshold during the predetermined period of detection, the transition timing specifying circuit 80 specifies ordinary transition timing set in advance, and outputs the specified result to the system control circuit 70. In another case, the transition timing specifying circuit 80 specifies step transition timing based on the decrease rate of the intensity ratio A and the correspondence information, and also outputs it to the system control circuit 70. In the correspondence information, the decrease rate of the intensity ratio A is associated with the time required for reaction.

(Third Function)

The transition timing specifying circuit 80 has the third function for estimating the timing at which the time-series variation of the intensity of the output light L2 converges by regressing the degree of the variation in the intensity. As with the second function, the third function is capable of specifying the transition timing from one step to another based on the decrease phase. One example is described with reference to FIG. 4. As described above, the time-series variation of the intensity ratio A in each step represented by each partial curve of the curve 301 converges to a predetermined value after the decrease phase and the convergence phase. This partial curve is not linear, and therefore curve fitting is applied to estimate the timing of convergence from the initial value of the partial curve. The transition timing specifying circuit 80 specifies the reaction progress degree from the convergence timing (convergence time) estimated. For example, the transition timing specifying circuit 80 specifies the convergence time from the convergence timing estimated, and specifies the reaction progress degree based on the length of the convergence time. Then, the step transition timing can be specified in the same manner as the second function. Information of a curve used for the curve fitting is stored in the memory circuit in advance. The curve is set as appropriate from data obtained experimentally. The transition timing specifying circuit 80 selects a curve used for the curve fitting as appropriate based on the initial shape in the decrease phase of the intensity ratio A.

Otherwise, the specimen measurement apparatus 10 of this embodiment has the same configuration as that of the first embodiment.

(Operation of the Specimen Measurement Apparatus)

Described below is an example of the measurement flow performed by the specimen measurement apparatus 10 of this embodiment. In the measurement flow, for example, the lower magnetic field application step, the spontaneous precipitation step, the upper magnetic field application step, and the measurement step are performed in this order as in the first embodiment. The specimen measurement apparatus 10 of this embodiment obtains step transition timing based on the degree of the variation of the intensity of the output light L2, and makes the transition of steps based on the timing. The degree of the variation of the light intensity corresponds to the reaction progress degree. In the following, a description is given of the operation of the specimen measurement apparatus of this embodiment to change the step transition timing.

Example 1 for Changing Step Transition Timing

Figure 12:
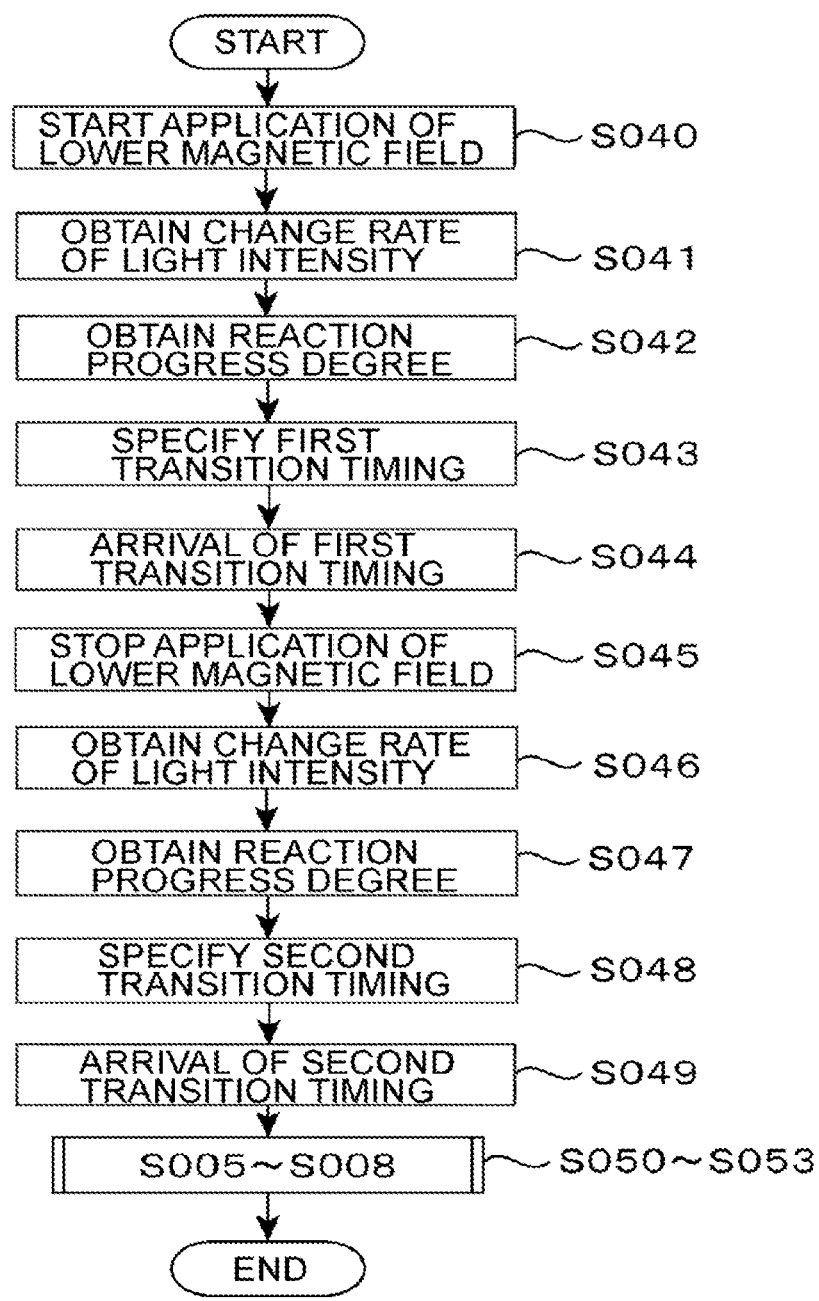
FIG. 12 is a flowchart of an example of the operation of a specimen measurement apparatus according to a second embodiment.

FIG. 12 is a flowchart of an example of the operation of the specimen measurement apparatus 10. When performing a process including a plurality of steps, the specimen measurement apparatus 10 specifies transition timing from one step to another based on the change rate of the intensity of the output light L2 in the step. The following description is made with reference to FIGS. 4 to 7 and 9 as appropriate.

First, a lower magnetic field is started to be applied to the reaction space 102 (step S040). As illustrated in FIG. 9, the application of the lower magnetic field is started at the time $t=t_0$.

Next, the transition timing specifying circuit 80 specifies and obtains the change rate of the light intensity based on time-series information of the intensity of the output light L2 obtained in the lower magnetic field application step $S_1$ (Step S041). Further, the transition timing specifying circuit 80 specifies and obtains the degree of the progress of the antibody-antigen reaction from the change rate of the light intensity obtained (step S042). The transition timing specifying circuit 80 specifies the degree of the progress of the antibody-antigen reaction in the reaction space 102 using the second and third functions described above.

The transition timing specifying circuit 80 specifies the reaction progression time $t_G$ sufficient for transition from the lower magnetic field application step $S_1$ based on the degree of the progress of the antibody-antigen reaction obtained in step S042. Then, the transition timing specifying circuit 80 specifies the time when the time $t_G$ has elapsed from the time $t_0$ as the first transition timing (step S043). When the time $t_G=t_1-t_0$, the transition timing is the time $t_1$ as illustrated in FIG. 9. Incidentally, the time $t_G$ is not limited to this, and may be shorter than a period $t_1-t_0$. The first transition timing is output to the system control circuit 70, and stored in a temporary memory circuit (not illustrated) or the like.

When the first transition timing arrives after a lapse of time from the time $t_0$ (step S044), the system control circuit 70 instructs the lower magnetic field applicator 40$d$ to stop driving. Upon receipt of the instruction, the lower magnetic field applicator 40$d$ stops driving. With this, the application of the lower magnetic field to the reaction space 102 ends (step S045). In other words, a step transition occurs from the lower magnetic field application step $S_1$ to the spontaneous precipitation step $T_1$.

Next, the transition timing specifying circuit 80 obtains the change rate of the light intensity based on time-series information of the intensity of the output light L2 obtained in the spontaneous precipitation step $T_1$ (step S046). Further, the transition timing specifying circuit 80 obtains the reaction progress degree from the change rate of the light intensity obtained (step S047).

For example, as in the same manner as in steps S041 to S044 described above, the transition timing specifying circuit 80 specifies the progression time $t_H$ sufficient for transition from the spontaneous precipitation step $T_0$, and specifies the time when the time $t_H$ has elapsed from the time $t_2$ as the second transition timing (step S048). When the time $t_H=t_4-t_2$, the transition timing is the time $t_9$ as illustrated in FIG. 9. Incidentally, the time $t_H$ is not limited to this, and may be shorter than a period $t_4-t_2$. The second transition timing is output to the system control circuit 70, and stored in a temporary memory circuit (not illustrated) or the like.

When the second transition timing arrives after a lapse of time from the time $t_2$ (step S049), the system control circuit 70 instructs the upper magnetic field applicator 40$u$ to start driving. With this, the application of the upper magnetic field to the reaction space 102 starts. Thereafter, the same process as steps S005 to S008 in FIG. 8 follows. Thereby, the amount of the antigen 14 retained in the reaction space 102 can be obtained (steps S050 to S053).

As described above, based on the change rate (decrease rate) of the intensity of the output light L2 in the lower magnetic field application step $S_1$, the state of the movement of the solid dispersion elements 9 due to the lower magnetic field is specified, and the first transition timing is obtained from the state. In this case, the movement state of the solid dispersion elements 9 due to the lower magnetic field is specified by, for example, as follows. As illustrated in FIG. 5C, in the lower magnetic field application step $S_1$, the solid dispersion elements 9 sometimes bind via the antigen 14 to a portion of the sensing surface 101 not along the magnetic lines b. If a large amount of the solid dispersion elements 9 are binding, the antibody-antigen reaction presumably progresses quickly. That is, the amount of binding elements corresponds to the degree of the progress of the antibody-antigen reaction. The amount of binding elements also corresponds to the decrease rate of the intensity of the output light L2. Accordingly, the decrease rate corresponds to the degree of the progress of the antibody-antigen reaction.

Besides, the solid dispersion elements 9 may be aggregated via the antigen 14 and form an aggregate. As the amount of aggregate increases, the aggregate becomes heavier, and its precipitation is promoted. This is likely to facilitate the entrance of the solid dispersion elements 9 in the sensing area 103. The amount of the aggregate corresponds to the concentration of the antigen 14, the first antibodies 6, and the second antibodies 13 in the reaction space 102. If the concentration is high, the antibody-antigen reaction presumably progresses quickly. That is, the amount of the aggregate corresponds to the degree of the progress of the antibody-antigen reaction. As the amount of the aggregate increases, in the reaction space 102, the solid dispersion elements 9 enter the sensing area 103 more easily, resulting in a rise in the decrease rate of the intensity of the output light L2. This also means that the decrease rate corresponds to the degree of the progress of the antibody-antigen reaction.

Further, based on the change rate (decrease rate) of the intensity of the output light L2 in the spontaneous precipitation step $T_1$, the degree of the progress of the antibody-antigen reaction between the antigen 14 and the antibody is specified, and the second transition timing is obtained from the degree. The antibody-antigen reaction between the antigen 14 and the antibody refers to a reaction where the first antibodies 6 fixed to the sensing surface 101 and the second antibodies 13 fixed to the solid dispersion elements 9 combine together via the antigen 14.

In this case, the degree of the progress of the antibody-antigen reaction is specified, for example, as follows. As illustrated in FIG. 6B, in the spontaneous precipitation step $T_1$, a plurality of the solid dispersion elements 9 precipitate toward the sensing surface 101. The solid dispersion elements 9 include those that precipitate spontaneously by gravity and those that bind to the sensing surface 101 by the antibody-antigen reaction. The amount of the solid dispersion elements 9 that bind to the sensing surface 101 is likely to correspond to the amount of the solid dispersion elements 9 that enter the sensing area 103 per unit time. Besides, as described above, the degree of the progress of the antibody-antigen reaction is also likely to correspond to the amount of an aggregate formed of the solid dispersion elements 9 that are aggregated via the antigen 14. Therefore, in the spontaneous precipitation step $T_1$, the degree of the progress of the antibody-antigen reaction can be specified from the change rate (decrease rate) of the intensity of the output light L2.

The first and second transition timings are "suitable timing" specified based on the degree of the progress of the antibody-antigen reaction. The specimen measurement apparatus 10 operates so that a transition occurs between steps based on the suitable timing. Thus, for example, the measurement can be accelerated. Besides, in the operation illustrated by the flowchart, the determination in step S021 may be skipped. In this case, it may be determined whether to perform the ordinary measurement based on the reaction progress degree obtained in step S027.

The transition timing specifying circuit 80 may obtain the first and second transition timings based on the reaction progress degree obtained in the lower magnetic field application step $S_1$.

Example 2 for Changing Step Transition Timing

Figure 13:
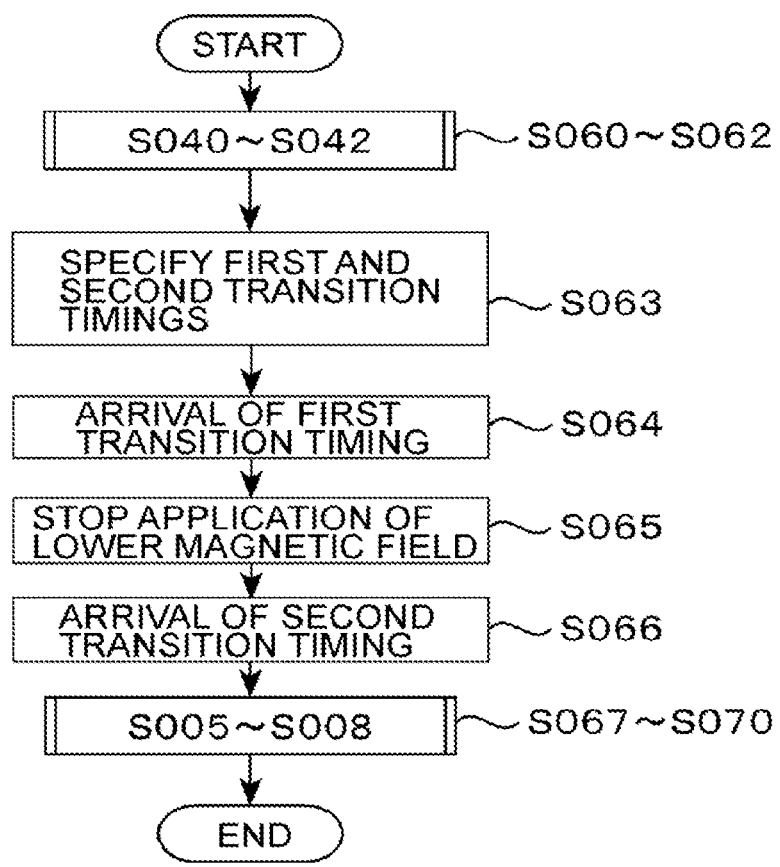
FIG. 13 is a flowchart of still another example of the operation of the specimen measurement apparatus in the second embodiment.

FIG. 13 is a flowchart of an example of the operation of the specimen measurement apparatus 10 to measure the amount of the antigen 14 contained in a sample liquid. When performing a process including a plurality of steps, the specimen measurement apparatus 10 specifies the state of the movement of the solid dispersion elements 9 and the reaction progress degree based on the change rate (decrease rate) of the intensity of the output light L2 in at least part of the state change step. As in the first embodiment, the state of the movement of the solid dispersion elements 9 may be obtained from the change rate (decrease rate) of the intensity of the output light L2. From the state of the movement of the solid dispersion elements 9 and the reaction progress degree thus obtained, the specimen measurement apparatus 10 specifies transition timing from the step and/or a step subsequent thereto. The following description is made with reference to FIGS. 4 to 7 and 9 as appropriate.

Before the start of a measurement, the transition timing specifying circuit 80 operates in the same manner as in steps S040 to S042 in the flowchart of FIG. 12 (steps S060 to S062).

Next, the transition timing specifying circuit 80 obtains the first and second transition timings (step S063). From the state of the movement of the solid dispersion elements 9 and the reaction progress degree obtained in step S063, the transition timing specifying circuit 80 specifies the time $t_G$ and the time $t_H$. Then, the transition timing specifying circuit 80 specifies the time when the time $t_G$ has elapsed from the time $t_0$ as the first transition timing. In addition, the transition timing specifying circuit 80 specifies the time when the time $t_H$ has elapsed from the time $t_2$ as the second transition timing.

When the first transition timing arrives after a lapse of time from the start of the measurement (step S064), the application of the lower magnetic field to the reaction space 102 ends (step S065).

When the second transition timing arrives after a lapse of time from the time $t_2$ (step S066), the system control circuit 70 instructs the upper magnetic field applicator 40u to start driving. With this, the application of the upper magnetic field to the reaction space 102 starts. Thereafter, the same process as steps S005 to S008 in FIG. 8 follows. Thereby, the amount of the antigen 14 retained in the reaction space 102 can be obtained (steps S067 to S070).

The transition timing specifying circuit 80 may obtain the first and second transition timings based on the state of the movement of the solid dispersion elements 9 obtained in the lower magnetic field application step $S_1$.

As described above, in this example, the first and second transition timings are obtained from the change rate (decrease rate) of the intensity of the output light L2 in the lower magnetic field application step $S_1$. Thus, it is possible to skip the process of obtaining the second transition timing in the spontaneous precipitation step $T_1$.

Example 3 for Changing Step Transition Timing

Figure 14:
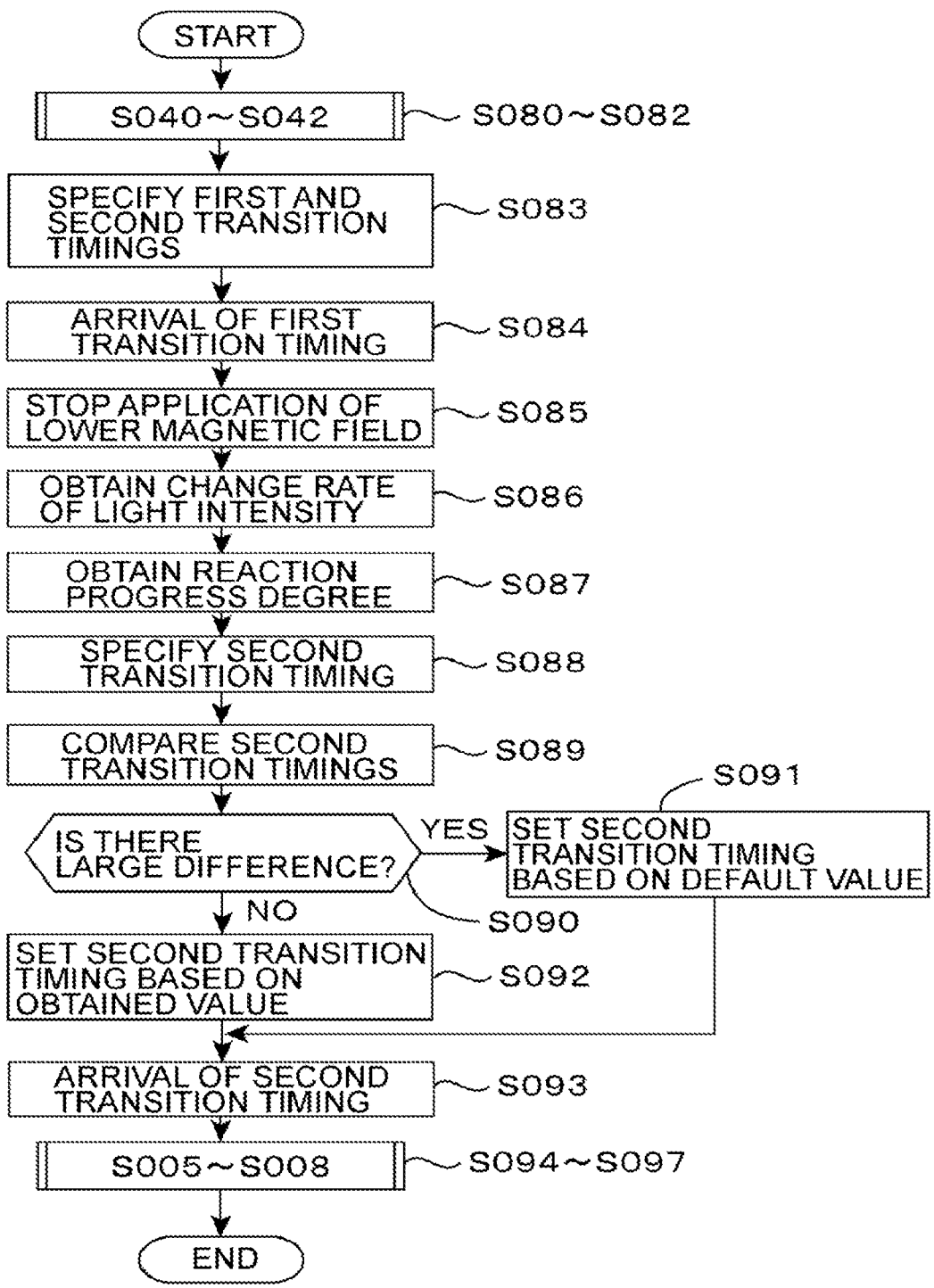
FIG. 14 is a flowchart of an example of the operation of a specimen measurement apparatus according to a third embodiment.

FIG. 14 is a flowchart of another example of the operation of the specimen measurement apparatus 10 to measure the amount of the antigen 14 contained in a sample liquid. When performing a process including a plurality of steps, the specimen measurement apparatus 10 determines transition timing from the step and a step subsequent thereto based on the change rate of the intensity of the output light L2 in at least part of the state change step. Further, in the subsequent step, the specimen measurement apparatus 10 determines transition timing from the subsequent step separately, and compares it with the transition timing previously determined. The specimen measurement apparatus 10 changes the transition timing from the subsequent step based on the comparison result. The following description is made with reference to FIGS. 4 to 7 and 9 as appropriate.

Before the start of a measurement, the transition timing specifying circuit 80 and the determination circuit 85 operate in the same manner as in steps S040 to S042 in the flowchart of FIG. 12 (steps S080 to S082). From the state of the movement of the solid dispersion elements 9 and the degree of the progress of the antibody-antigen reaction, the transition timing specifying circuit 80 specifies progression time $t_{H1}$ sufficient for transition from the spontaneous precipitation step $T_0$. Then, the transition timing specifying circuit 80 determines the time when the time $t_{H1}$ has elapsed from the time $t_2$ as the second transition timing (step S083). Hereinafter, the second transition timing determined in step S083 may sometimes be referred to as "second transition timing (a)".

When the first transition timing arrives after a lapse of time from the start of the measurement (step S084), the application of the lower magnetic field to the reaction space 102 ends (step S085).

Next, the transition timing specifying circuit 80 obtains the change rate of the light intensity based on time-series information of the intensity of the output light L2 obtained in the spontaneous precipitation step $T_1$ (Step S086). Further, the transition timing specifying circuit 80 obtains the state of the movement of the solid dispersion elements 9 and the degree of the progress of the antibody-antigen reaction from the change rate of the light intensity obtained (step S087). The transition timing specifying circuit 80 specifies the second transition timing based on the degree of the progress of the antibody-antigen reaction and the like (step S088). Hereinafter, the second transition timing determined in step S088 may sometimes be referred to as "second transition timing (b)". From the degree of the progress of the antibody-antigen reaction and the like, the transition timing specifying circuit 80 specifies progression time $t_{H2}$ sufficient for transition from the spontaneous precipitation step $T_1$. Then, the transition timing specifying circuit 80 determines the time when the time $t_{H2}$ has elapsed from the time $t_2$ as the second transition timing (b).

The transition timing specifying circuit 80 compares the two second transition timings (step S089). If there is a large difference between the second transition timing (a) and the second transition timing (b) (YES in step S090), the second transition timing is set based on a default value (step S091). The default value can be specified from time $t_D$ required for the ordinary spontaneous precipitation step $T_0$. That is, in this case, the second transition timing is set as $t=t_2+t_D$. The time $t_D$ is stored in the memory circuit 90 in advance.

On the other hand, if there is no large difference between the second transition timing (a) and the second transition timing (b) (NO in step S090), the second transition timing is set based on either or both of the two second transition timings (step S092). In this case, for example, the second transition timing (b) is set as the second transition timing.

The average of the second transition timings (a) and (b) may be set as the second transition timing.

When the second transition timing arrives after a lapse of time from the time $t_2$ (step S093), the system control circuit 70 starts the application of the upper magnetic field. Thereafter, the same process as steps S005 to S008 in FIG. 8 follows. Thereby, the amount of the antigen 14 retained in the reaction space 102 can be obtained (steps S094 to S097).

As described above, the first transition timing and the second transition timing (a) are obtained in the lower magnetic field application step $S_1$, and the second transition timing (b) is obtained in the spontaneous precipitation step $T_1$. The second transition timing is set based on the second transition timing (a) and the second transition timing (b). That is, when there is a large difference between the second transition timing (a) and the second transition timing (b), this is considered as an error, and the second transition timing is determined based on the default set in advance. This increases the accuracy of the second transition timing.

Otherwise, the specimen measurement apparatus 10 of the embodiment may operate in the same manner as in the first embodiment. In addition, in the first embodiment, the second time (measurement available time) may be estimated using the second and third functions of the embodiment.

As a modification, the specimen measurement apparatus 10 of the embodiment may further include the determination circuit 85. As described above, the determination circuit 85 determines whether a test item to be measured is a specific test item. In this case, the specimen measurement apparatus 10 determines whether the test item is a specific test item by the process of steps S020 to S023 illustrated in FIG. 11. If the determination result is that the test item is a specific test item, a process illustrated in any one of FIGS. 12 to 14 is performed.

According to the second embodiment, focusing on the reaction progress degree between a test substance and a reagent, the specimen measurement apparatus 10 is configured to obtain the degree of the progress of the antibody-antigen reaction between the antigen 14 and an antibody based on the change rate of the intensity of the output light L2. The specimen measurement apparatus 10 is further configured to specify, from the degree of the progress of the antibody-antigen reaction and the like, the time at which the antibody-antigen reaction has progressed to a level that guarantees the measurement accuracy or the time at which the measurement accuracy is guaranteed and determine the time as the step transition timing. The step transition timing includes transition timing from a current step and also transition timing from a subsequent step. Here, the state where the antibody-antigen reaction has progressed to a level that guarantees the measurement accuracy includes the state where qualitative measurement and quantitative measurement can be performed. Therefore, the specimen measurement apparatus 10 of this embodiment can make a transition from one step to another before the completion of the precipitation of the solid dispersion elements 9. Further, since a measurement is performed at the time when the reaction has progressed to a level at least sufficient to perform the measurement, the measurement accuracy can be guaranteed even if the transition timing is put forward.

Third Embodiment

The specimen measurement apparatus 10 of a third embodiment is of basically the same configuration as that of the first embodiment. Therefore, the specimen measurement apparatus 10 of this embodiment is described with reference to FIG. 1 as appropriate. The specimen measurement apparatus 10 of this embodiment operates similarly to that of the second embodiment except that it estimates concentration information (concentration range) of a test substance from the reaction progress degree between the test substance and a reagent (or the state of the movement of the solid dispersion elements 9), and specifies the step transition timing based on the estimation result. When only the concentration information of the test substance is unknown, the specimen measurement apparatus 10 estimates concentration information (concentration range) based on a time-series variation in the intensity of the output light L2, and specifies the step transition timing based on the estimation result.

<Transition Timing Specifying Circuit>

The transition timing specifying circuit 80 estimates the concentration of a test substance based on the reaction progress degree between the test substance and a reagent and the like, and specifies the step transition timing based on the specified result. The reaction progress degree and the like may be obtained in the same manner as in the second embodiment. Here, the "concentration" includes the value of the concentration and a range of the value of the concentration. For example, assuming that the test substance is the antigen 14 and the reagent is an antibody, the transition timing specifying circuit 80 can estimate the concentration of the antigen 14 from the degree of the progress of the antibody-antigen reaction between them and the like. For example, the transition timing specifying circuit 80 has a fourth function for this specifying process. The transition timing specifying circuit 80 can also estimate the concentration of the antigen 14 from the steady-state value of the output light L2. For example, the transition timing specifying circuit 80 has a fifth function for this estimation.

The second and third functions are capable of specifying the degree of the progress of the antibody-antigen reaction based on a time-series variation in the light intensity ratio. The fourth and fifth functions pay attention to the concentration of the antigen 14 in the parameters to specify the degree of the progress of the antibody-antigen reaction and the like.

(Fourth Function)

The fourth function is used to estimate the concentration of the antigen 14 in the reaction space 102 from the degree of the progress of the antibody-antigen reaction therein and the like. Examples of parameters to determine the degree of the progress of the antibody-antigen reaction and the like (hereinafter sometimes simply referred to as "parameter") include the concentration of the antibody and the concentration of the antigen. To compare the measurement results of a plurality of measurements, the measurements are performed with the same values of parameters except the concentration of the antigen, for example. With this, the concentration ratio of the antigen 14 can be obtained from the change rate (decrease rate) of the intensity of the output light L2. The concentration ratio is, for example, a ratio of the concentration to a reference concentration set in advance. The actual concentration of the antigen 14 in the reaction space 102 can be obtained from the concentration ratio and the reference concentration. Correspondence information between the change rate (decrease rate) of the intensity of the output light L2 and the concentration of the antigen 14 may be empirically and experimentally obtained, and stored in the memory circuit 90 or the like in advance. In this case, the transition timing specifying circuit 80 can estimate the concentration of the antigen 14 based on the correspondence information. The correspondence information may indicate the correspondence between the degree of the progress of the antibody-antigen reaction and the like and the concentration of the antigen 14. The correspondence information may be obtained by, for example, measuring a plurality of sample liquids in which the concentration of the antigen 14 is known and deriving the correspondence relationship from the measurement results. Examples of the correspondence information obtained include a correspondence table between the change rate of the intensity of the output light L2 and the concentration of the antigen 14, and a calibration curve with the horizontal axis indicating the change rate of the intensity of the output light L2 and the vertical axis indicating the concentration of the antigen 14.

The concentration of the antigen 14 in the reaction space tends to increase as the change rate (decrease rate) of the intensity of the output light L2 rises. As the concentration of the antigen 14 increases, the antigen 14 binds to the antibody with a higher probability. Accordingly, the antibody-antigen reaction progresses faster. The fast progress of the antibody-antigen reaction reduces the time (the second time) taken until the antibody-antigen reaction becomes steady in the reaction space 102. Thus, the step transition timing can be put forward as compared to the ordinary measurement.

(Fifth Function)

The fifth function is used to estimate the concentration of the antigen 14 in the reaction space 102 from the steady-state value of the output light L2. To compare the measurement results of a plurality of measurements, in this case also, the measurements are performed with the same values of parameters except the concentration of the antigen. With this, the concentration ratio of the antigen 14 can be obtained from the steady-state value of the output light L2. The concentration ratio is, for example, a ratio of the concentration to a reference concentration set in advance. The steady-state value of the output light L2 may include, for example, a first steady-state value and a second steady-state value. Correspondence information between the steady-state value of the output light L2 and the concentration of the antigen 14 may be empirically and experimentally obtained, and stored in the memory circuit 90 or the like in advance. In this case, the transition timing specifying circuit 80 can estimate the concentration of the antigen 14 based on the correspondence information. The correspondence information may be obtained by, for example, measuring a plurality of sample liquids in which the concentration of the antigen 14 is known and deriving the correspondence relationship from the measurement results. Examples of the correspondence information obtained include a correspondence table between the first steady-state value and the concentration of the antigen 14, and a calibration curve with the horizontal axis indicating the first steady-state value and the vertical axis indicating the concentration of the antigen 14. The transition timing specifying circuit 80 can obtain the concentration ratio of the antigen 14 also from the convergence timing (convergence time) estimated. For example, the transition timing specifying circuit 80 specifies the convergence time from the convergence timing estimated, and specifies the concentration ratio of the antigen 14 based on the length of the convergence time.

(Comparison of Curves According to the Concentration of Antigen)

FIG. 15 is a graph 42 illustrating a time-series variation in the intensity of the output light L2 detected in the measurement. In FIG. 15, a dashed curve 304 corresponds to a measurement when the concentration of the antigen 14 is zero in the reaction space 102, while the solid curve 301 corresponds to a measurement when the concentration of the antigen 14 is high in the reaction space 102. The curve 301 corresponds to the curve 301 of FIG. 4. In addition, a dashed-dotted curve 303 corresponds to a measurement when the concentration of the antigen 14 is low in the reaction space 102. When the concentration of the antigen 14 is low, the concentration is above zero and below the concentration corresponding to the curve 301. The value of this concentration is, for example, a half of the concentration corresponding to the curve 301.

The measurements corresponding to the three curves are performed using parameters of the same value except the concentration of the antigen 14. Further, the step transition timings in the measurements are set at the same time. At this time, the degree of the progress of the antibody-antigen reaction and the like corresponds to the concentration of the antigen 14. The correspondence relationship is described in comparison of the shapes of the curves 301, 303, and 304 in each step.

(Lower Magnetic Field Application Step)

As an example of the fourth function, the transition timing specifying circuit 80 compares the average decrease rates of the intensity ratio A in the decrease phase of the lower magnetic field application step $S_0$. The decrease phase is, for example, a period $t_0$ to $t_1$. The initial phase can be set within the period $t_0$ to $t_1$. The period of this phase is, for example, $t_0$ to $t_P$ described above.

In the initial phase, the average decrease rate indicated by the curve 301 is higher than that indicated by the curve 304. The average decrease rate indicated by the curve 303 is between those indicated by the curves 301 and 304. That is, as the concentration of the antigen 14 increases in the reaction space 102, the average decrease rate of the intensity ratio A rises in the period $t_0$ to $t_1$. This means that the higher the concentration of the antigen 14 is, the faster the antibody-antigen reaction progresses. In this step, the solid dispersion elements 9 that enter the sensing area 103 are only those arrayed along the magnetic lines b (corresponding to the application of the lower magnetic field, see FIG. 5A, etc.) in the measurement corresponding to the curve 304. On the other hand, in the measurements corresponding to the curves 301 and 303, the solid dispersion elements 9 that are attracted to the sensing surface 101 by the antibody-antigen reaction also enter the sensing area 103.

As a result, when the antigen 14 is retained in the reaction space 102, more amount of the solid dispersion elements 9 enter the sensing area 103 per unit time. Accordingly, the average decrease rate indicated by the curves 301 and 303 is higher than that indicated by the curve 304. In addition, since the concentration of the antigen 14 is high in the measurement corresponding to the curve 301, more amount of the solid dispersion elements 9 enter the sensing area 103 per unit time as compared to the measurement corresponding to the curve 303. Therefore, the antibody-antigen reaction progresses faster, resulting in that the average decrease rate indicated by the curve 301 is higher than that indicated by the curve 303.

As an example of the fifth function, the transition timing specifying circuit 80 compares the first steady-state values in the lower magnetic field application step $S_0$. Each curve converges to the first steady-state value after the decrease phase and the convergence phase. At the time $t_2$, the curve 301 converges to the intensity ratio $A_{11}$ as the first steady-state values thereof. The curve 303 also converges to the intensity ratio $A_{21}$ as the first steady-state values thereof. The curve 304 also converges to the intensity ratio $A_{31}$ as the first steady-state values thereof. At this time, the values of the intensity ratio A are represented as $A_{11} < A_{21} < A_{31}$. That is, as the concentration of the antigen 14 increases in the reaction space 102, the intensity ratio A corresponding to the first steady-state value decreases. This means that the higher the concentration of the antigen 14 is, the more amount of the solid dispersion elements are present in the sensing area 103 in the steady state. Here, the steady state refers to the state where the solid dispersion elements 9 are considered to no longer enter the sensing area 103.

At the time $t_2$, presumably, almost the same amount of the solid dispersion elements 9 are arrayed along each of the magnetic lines b in the sensing area 103. That is, the difference between the first steady-state values corresponds to the amount of the solid dispersion elements 9 except those arrayed along the magnetic lines b. The solid dispersion elements 9 include those binding to the sensing surface 101 via the antigen 14. As the solid dispersion elements 9 are bound by the lower magnetic field, they are stacked upward. Therefore, the amount of the solid dispersion elements 9 that have spontaneously precipitated in the sensing area 103 is likely to be little. That is, the difference corresponds to the amount of the solid dispersion elements 9 binding to the sensing surface 101. Accordingly, the amount of the solid dispersion elements 9 except those arrayed along the magnetic lines b is considered to correspond to the concentration of the antigen 14. In view of the above, the intensity ratio A corresponding to the first steady-state value decreases as the concentration of the antigen 14 increases because of an increase in the amount of the solid dispersion elements 9 binding to the sensing surface 101.

Besides, the concentration of the antigen 14 in the reaction space 102 may be obtained regarding the value of the intensity ratio A at the time $t_1$ as the first steady-state value. In the case where the concentration of the antigen 14 is obtained from this value based on correspondence information, information on the concentration of the antigen 14 corresponding to the intensity ratio A at the time $t_1$ is experimentally obtained and stored in the memory circuit 90 in advance.

(Spontaneous Precipitation Step)

As another example of the fourth function, the transition timing specifying circuit 80 compares the average decrease rates of the intensity ratio A in the decrease phase of the spontaneous precipitation step $T_0$. The decrease phase is, for example, a period $t_3$ to $t_4$. The initial phase can be set within the period $t_3$ to $t_4$. The period of this phase is, for example, $t_3$ to $t_Q$ described above.

In the spontaneous precipitation step $T_0$, the average decrease rates indicated by the curves are in the same relationship as in the lower magnetic field application step $S_0$. That is, as the concentration of the antigen 14 increases in the reaction space 102, the average decrease rate of the intensity ratio A rises in the period $t_3$ to $t_4$. This means that the higher the concentration of the antigen 14 is, the more amount of the solid dispersion elements 9 enter the sensing area 103 per unit time. From this, it is understood that, in this case also, the higher the concentration of the antigen 14 is, the faster the antibody-antigen reaction progresses.

As another example of the fifth function, the transition timing specifying circuit 80 compares the second steady-state values in the spontaneous precipitation step $T_0$. Each curve converges to the second steady-state value after the decrease phase and the convergence phase. At this time, the values of the intensity ratio A are represented as $A_{13}<A_{23}<A_{33}$. That is, in this case also, as the concentration of the antigen 14 increases in the reaction space 102, the intensity ratio A corresponding to the second steady-state value decreases. This means that the higher the concentration of the antigen 14 is, the more amount of the solid dispersion elements are present in the sensing area 103 in the steady state.

One reason is that, in the steady state, when the concentration of the antigen 14 is high in the reaction space 102, the sensing area 103 is filled with the solid dispersion elements 9 at a high rate. As illustrated in FIG. 6C, when the concentration of the antigen 14 is high in the reaction space 102, the solid dispersion elements 9 specifically bind to the sensing surface 101 in sequence. As a result, the solid dispersion elements 9 are distributed uniformly on the sensing surface 101. Further, the solid dispersion elements 9 are more likely to aggregate together via the antigen 14. Therefore, there are less spaces between accumulations of the solid dispersion elements 9 generated in the sensing area 103. On the other hand, when the antigen 14 is not retained in the reaction space 102, the solid dispersion elements 9 do not specifically bind to the sensing surface 101. Accordingly, the solid dispersion elements 9 are less likely to be distributed uniformly on the sensing surface 101. Besides, the solid dispersion elements 9 aggregated together may sometimes form secondary particles. Therefore, in this case, there are more spaces between accumulations of the solid dispersion elements 9 generated in the sensing area 103. For these reasons, when the concentration of the antigen 14 is high in the reaction space 102, the sensing area 103 is filled with the solid dispersion elements 9 at a high rate.

Besides, the concentration of the antigen 14 in the reaction space 102 may be obtained regarding the value of the intensity ratio A at the time $t_3$ as the second steady-state value. In the case where the concentration of the antigen 14 is obtained from the second steady-state value based on correspondence information, information on the concentration of the antigen 14 corresponding to the intensity ratio A at the time $t_3$ is experimentally obtained and stored in the memory circuit 90 in advance.

The transition timing specifying circuit 80 may perform a variety of corrections. For example, when comparing measurement results in which different values are used for a parameter other than the concentration of the antigen 14, the transition timing specifying circuit 80 performs a predetermined correction to enable the comparison of the measurement results. For example, if temperature changes during the measurements, the transition timing specifying circuit 80 may correct the temperature in the measurement result obtained based on the temperature change and information indicating the effects of the temperature.

Otherwise, the specimen measurement apparatus 10 of this embodiment has the same configuration as that of the first or the second embodiment.

(Operation of the Specimen Measurement Apparatus)

FIG. 16 is a flowchart of an example of the operation of the specimen measurement apparatus 10 to measure the amount of the antigen 14 contained in a sample liquid. When performing a process including a plurality of steps, the specimen measurement apparatus 10 estimates the concentration of the antigen 14 in the reaction space 102 from the change rate of the intensity of the output light L2 in the step. The specimen measurement apparatus 10 determines transition timing from the step and/or a step subsequent thereto based on the concentration of the antigen 14. The following description is made with reference to FIGS. 4 to 7 and 9 as appropriate.

Before the start of measurement, the transition timing specifying circuit 80 acquires the test information for a measurement to be performed. This information includes information other than the concentration of the antigen 14.

This information may be, for example, parameters related to the reaction progress degree and the like. Thereby, parameters except the concentration of the antigen 14 are obtained from the test information.

Having obtained the test information (step S100), the system control circuit 70 starts the measurement flow (step S101). This measurement is performed under constant temperature conditions. If not, the measurement temperature is sequentially measured and stored. When the measurement flow starts, the application of the lower magnetic field to the reaction space 102 starts (step S102).

Next, the transition timing specifying circuit 80 obtains the change rate of the light intensity based on time-series information of the intensity of the output light L2 obtained in the lower magnetic field application step $S_1$ (step S103). Further, the transition timing specifying circuit 80 estimates the concentration of the antigen 14 in the reaction space 102 from the change rate of the light intensity obtained (step S104). The transition timing specifying circuit 80 estimates the concentration of the antigen 14 in a manner, for example, as follows. First, the transition timing specifying circuit 80 obtains the degree of the progress of the antibody-antigen reaction from the change rate of the light intensity obtained. This process may be performed in the same manner as in step S043 in the flowchart of FIG. 12 using the second or the third function.

Then, the transition timing specifying circuit 80 obtains the concentration of the antigen 14 in the reaction space 102 using, for example, the fourth function based on the degree of the progress of the antibody-antigen reaction. At this time, the transition timing specifying circuit 80 uses the test information obtained in step S100. For example, the transition timing specifying circuit 80 extracts an association rate coefficient and a dissociation rate coefficient in the antibody-antigen reaction from parameters contained in the test information to obtain the concentration. By removing the effects caused by parameters other than the concentration of the antigen 14 from the degree of the progress of the antibody-antigen reaction, the concentration of the antigen 14 in the reaction space 102 can be specified. As described above, the concentration includes concentration ratio, concentration range, and the like.

Thereafter, the transition timing specifying circuit 80 obtains the first transition timing (step S105). From the concentration of the antigen 14 obtained in step S104, the transition timing specifying circuit 80 specifies the time $t_G$. For example, the time $t_G$ may be specified based on the correspondence information mentioned above. The transition timing specifying circuit 80 specifies the time when the time $t_G$ has elapsed from the time $t_0$ as the first transition timing.

When the first transition timing arrives after a lapse of time from the start of the measurement (step S106), the application of the lower magnetic field to the reaction space 102 ends (step S107).

Next, the transition timing specifying circuit 80 obtains the change rate of the light intensity based on time-series information of the intensity of the output light L2 obtained in the spontaneous precipitation step $T_1$ (Step S108). Further, the transition timing specifying circuit 80 estimates the concentration of the antigen 14 in the reaction space 102 from the change rate of the light intensity obtained (step S109). The transition timing specifying circuit 80 may estimate the concentration of the antigen 14 in the same manner as in step S104 described above. As described above, the concentration includes concentration ratio, concentration range, and the like.

Thereafter, the transition timing specifying circuit 80 obtains the second transition timing (step S110). From the concentration of the antigen 14 obtained in step S104, the transition timing specifying circuit 80 specifies the time $t_H$. For example, the time $t_H$ may be specified based on the correspondence information mentioned above. The transition timing specifying circuit 80 specifies the time when the time $t_H$ has elapsed from the time $t_2$ as the second transition timing.

When the second transition timing arrives after a lapse of time from the time $t_2$ (step S111), the system control circuit 70 starts the application of the upper magnetic field. Thereafter, the same process as steps S005 to S008 in FIG. 8 follows. Thereby, the amount of the antigen 14 retained in the reaction space 102 can be obtained (steps S112 to S115).

As described above, in this example, based on the change rate of the intensity of the output light L2 in the lower magnetic field application step $S_1$, the concentration of the antigen 14 is estimated. The first transition timing is obtained from the concentration. In addition, based on the change rate of the intensity of the output light L2 in the spontaneous precipitation step $T_1$, the concentration of the antigen 14 is estimated. The second transition timing is obtained from the concentration. In other words, in the flowchart of FIG. 12, instead of the degree of the progress of the antibody-antigen reaction, the concentration of the antigen 14 is used as a parameter to determine the transition timing. The degree of the progress of the antibody-antigen reaction varies according to factors other than the concentration. Accordingly, by removing the factors from the degree of the progress of the antibody-antigen reaction, the concentration of the antigen 14 can be obtained. Thus, the transition timing specifying circuit 80 can obtain the first and second transition timings based on the concentration of the antigen 14 thus obtained.

In the flowcharts of FIGS. 13 and 14 for the second embodiment, instead of the reaction progress degree, the concentration of the antigen 14 may be used as a parameter to specify the transition timing. In this manner, the operation of the specimen measurement apparatus 10 of this embodiment may be appropriately combined with that of the second embodiment. Besides, in the process illustrated by the flowcharts, the step transition timing may be specified using the fifth function. That is, instead of the reaction progress degree, the steady-state value may be used as a parameter to specify the transition timing. Further, in the first embodiment, the second time may be estimated using the concentration of the antigen 14.

The specimen measurement apparatus 10 of this embodiment can estimate the concentration of the antigen 14 in the reaction space 102 based on the change rate of the intensity of the output light L2. Therefore, when a test item to be measured is a specific test item, if the estimated value of the concentration exceeds a predetermined value, the step transition may be made at this point. Further, the estimated value of the concentration may be employed for the determination in the measurement.

According to the third embodiment, focusing on the concentration of the antigen 14 in the reaction space 102, the specimen measurement apparatus 10 is configured to estimate the concentration of the antigen 14 based on the change rate of the intensity of the output light L2. The specimen measurement apparatus 10 is further configured to specify, from the concentration of the antigen 14, the time at which the antibody-antigen reaction is completed as the step transition timing. Therefore, the specimen measurement apparatus 10 of this embodiment can make a transition from one step to another before the completion of the precipitation of the solid dispersion elements 9. Further, since a measurement is performed at the time when the reaction has progressed to a level at least sufficient to perform the measurement, the measurement accuracy can be guaranteed even if the transition timing is put forward.

According to the embodiments, the measurement flow includes the lower magnetic field application step, the spontaneous precipitation step, the upper magnetic field application step, and the measurement step. However, the measurement flow is not so limited, and it need not necessarily include the lower magnetic field application step. In this case, the spontaneous precipitation step, the upper magnetic field application step, and the measurement step are performed in this order from the start of a measurement. In this measurement flow also, the step transition timing described above can be changed.

According to the embodiments, the specimen measurement apparatus 10 is configured to specify the step transition timing based on a parameter obtained from a time-series variation in the intensity of the output light L2. Therefore, the time required for a step can be made variable depending on the type of a test item, the environment, and the like. Thus, it is possible to optimize the measurement time according to the parameter obtained from a time-series variation in the intensity of the output light L2.

Other Embodiments

In the above embodiments, an example is described in which the state of the inside of the reaction case 20 is changed by a magnetic field. However, this is not so limited. The state of the inside of the reaction case 20 may also be changed by heat, ultrasonic waves, or the like. In this case, for example, a heater or an ultrasonic transducer is employed. The heater applies heat to a sample liquid and a reagent in the reaction case 20 to raise their temperature. The ultrasonic transducer applies ultrasonic vibration to a sample liquid and a reagent in the reaction case 20 so that they flow in the reaction case 20 due to the ultrasonic vibration. In this manner, the state of the inside of the reaction case 20 can be changed by the application of heat or ultrasonic waves.

[Definition of Processor]

In the above embodiments, the various circuits such as the processing circuit 53, the information generating circuit 65, the system control circuit 70, the transition timing specifying circuit 80, and the determination circuit 85 are processors. The term processor as used herein refers to circuits including, for example, dedicated or general purpose central processing units (CPU), arithmetic circuits (circuitries), application specific integrated circuits (ASIC), programmable logic devices such as simple programmable logic devices (SPLD), complex programmable logic devices (CPLD), and field-programmable gate arrays (FPGA). Each of the processors loads a program stored in a memory or directly installed in the circuit of the processor and executes it to implement the functions. The processors may be provided with their respective memories for storing the program, or the memory circuit 90 illustrated in FIG. 1 or 10 may store programs each corresponding to the functions of each processor. Note that it is not necessary that a single circuit forms each of the processors of the embodiments. A plurality of independent circuits may be combined to form one processor that implements their functions. Further, the constituent elements illustrated in FIG. 1 or 10 may be integrated into one processor that implements their functions.

[Correspondence Between the Constituent Elements of the Claims and Those of the Embodiments]

The detector of the claims corresponds to the detector 50 of the embodiments. The control circuit of the claims corresponds to the various circuits of the embodiments such as the system control circuit 70, the transition timing specifying circuit 80, and the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A specimen measurement apparatus configured to cause a test substance contained in a sample liquid retained in a reaction container to react with a reagent, and perform a plurality of steps to measure properties of the test substance, the specimen measurement apparatus comprising:
 a detector configured to output electromagnetic waves to the reaction container and to detect an intensity of the electromagnetic waves that vary according to a state in the reaction container in time series;
 a transition timing specifying circuit configured to determine each of one or more convergence states associated with the detected intensity; and
 a control circuit configured to control transition timing between steps of the plurality of steps based on timing at which the transition timing specifying circuit determines each of the one or more convergence states associated with the intensity of the electromagnetic waves detected by the detector converges according to a corresponding one or more intensity convergence values.

2. The specimen measurement apparatus of claim 1, wherein the electromagnetic waves are light.

3. The specimen measurement apparatus of claim 1, wherein
 the control circuit is configured to specify the transition timing based on the timing at which the intensity of the electromagnetic waves converges, and make a transition from one step to another of the plurality of steps based on the transition timing specified.

4. The specimen measurement apparatus of claim 3, wherein the control circuit is configured to specify a point after a lapse of a predetermined time from the timing at which the intensity of the electromagnetic waves converges, as the transition timing.

5. The specimen measurement apparatus of claim 1, wherein
 the plurality of steps includes two or more state change steps to change the state in the reaction container, and
 the control circuit is configured to control the transition timing from one state change step to another state change step of the two or more state change steps.

6. The specimen measurement apparatus of claim 5, wherein the two or more state change steps include a magnetic field application step to change the state in the reaction container by a magnetic field.

7. The specimen measurement apparatus of claim 5, wherein the two or more state change steps include a heat application step to change the state in the reaction container by heat.

8. The specimen measurement apparatus of claim 5, wherein
the one state change step includes a detection step in which the detector detects an intensity of the electromagnetic waves, and
the control circuit is configured to control the transition timing from the one state change step to another state change step based on timing at which the intensity of the electromagnetic waves detected by the detector converges.

9. The specimen measurement apparatus of claim 5, wherein
the one state change step is a lower magnetic field application step to apply a lower magnetic field to a space inside the reaction container, and
another state change step is a spontaneous precipitation step to let at least the test substance spontaneously precipitate.

10. The specimen measurement apparatus of claim 5, wherein
the one state change step is a spontaneous precipitation step to let at least the test substance spontaneously precipitate, and
another state change step is an upper magnetic field application step to apply an upper magnetic field to a space inside the reaction container.

11. The specimen measurement apparatus of claim 5, wherein
the plurality of steps includes a first state change step, a second state change step, and a third state change step as the two or more state change steps, and
the control circuit is configured to control the transition timing from the first state change step to the second state change step, and the transition timing from the second state change step to the third state change step.

12. The specimen measurement apparatus of claim 11, wherein
the first state change step is a lower magnetic field application step to apply a lower magnetic field to a space inside the reaction container,
the second state change step is a spontaneous precipitation step to let at least the test substance spontaneously precipitate, and
the third state change step is an upper magnetic field application step to apply an upper magnetic field to the space inside the reaction container.

13. The specimen measurement apparatus of claim 1, wherein
one surface of the reaction container is formed of a main surface of a planar optical waveguide,
the reaction container is configured to retain a first substance that is fixed to the main surface to specifically bind to the test substance, and solid dispersion elements that carry a second substance that specifically binds to the test substance,
the detector is configured to output the electromagnetic waves such that the electromagnetic waves propagate through the planar optical waveguide, and detect the electromagnetic waves intensity of which varies in the planar optical waveguide, and
the control circuit is configured to change at least one of size of a force applied to the solid dispersion elements, an amount of time for which the force is applied to the solid dispersion elements, and a direction in which the force is applied to the solid dispersion elements based on timing at which the intensity of the electromagnetic waves detected by the detector converges.

* * * * *